US012721956B2

(12) United States Patent
Peng et al.

(10) Patent No.: US 12,721,956 B2
(45) Date of Patent: Sep. 1, 2026

(54) PRESSURIZED NEBULIZER

(71) Applicant: GUANGZHOU JUNLIN MEDICAL TECHNOLOGY CO., LTD., Guangzhou (CN)

(72) Inventors: Jun Peng, Guangzhou (CN); Wei Kang, Guangzhou (CN); Yulong Deng, Guangzhou (CN)

(73) Assignee: GUANGZHOU JUNLIN MEDICAL TECHNOLOGY CO., LTD., Guangzhou (CN)

(*) Notice: Subject to any disclaimer, the term of this patent is extended or adjusted under 35 U.S.C. 154(b) by 567 days.

(21) Appl. No.: 18/364,602

(22) Filed: Aug. 3, 2023

(65) Prior Publication Data

US 2023/0372639 A1 Nov. 23, 2023

(30) Foreign Application Priority Data

Feb. 8, 2023 (CN) ........................ 202310085133.2

(51) Int. Cl.
*A61M 11/00* (2006.01)
*A61M 13/00* (2006.01)

(52) U.S. Cl.
CPC ........ *A61M 11/006* (2014.02); *A61M 13/003* (2013.01)

(58) Field of Classification Search
CPC ..... A61M 11/006; A61M 13/00; F04B 43/12; B05B 9/042
See application file for complete search history.

(56) References Cited

U.S. PATENT DOCUMENTS

2024/0024613 A1* 1/2024 Novkov .............. A61M 16/022

FOREIGN PATENT DOCUMENTS

| | | | |
|---|---|---|---|
| CN | 204099169 | U | 1/2015 |
| CN | 208831209 | U | 5/2019 |
| CN | 209597462 | U | 11/2019 |
| CN | 112974010 | A | 6/2021 |
| CN | 214787923 | U | 11/2021 |
| EP | 0258901 | A2 | 3/1988 |

* cited by examiner

*Primary Examiner* — Bradley J Osinski
(74) *Attorney, Agent, or Firm* — SHIMOKAJI IP

(57) ABSTRACT

A pressurized nebulizer includes a nozzle, a peristaltic pump, and an elastic braided hose. The peristaltic pump includes a fixing part, a mating part, a rotating base and a roller. When the mating part and the fixing part are in a closed state, the elastic braided hose is arranged between the mating part and the fixing part, and between the mating part and the roller. An output end of the elastic braided hose is connected with the nozzle. The roller in the working stroke has a limit position of extruding the elastic braided hose to a limit state, a minimum clearance formed between the roller and the mating part is $1.5T \leq P \leq 1.9T$, where T denotes a unilateral wall thickness of the elastic braided hose, and P denotes the minimum clearance. The nebulizer can avoids liquid contact contamination, provide a stable output and have accurate accuracy.

18 Claims, 19 Drawing Sheets

(V denotes Cumulative Volume Distribution, N denotes Cumulative Quantity Distribution)

PRESSURIZED NEBULIZER

FIELD OF THE INVENTION

The present invention relates to the technical field of nebulizers, in particular to a pressurized nebulizer applied in a medical body cavity.

BACKGROUND OF THE INVENTION

It is well known that intraperitoneal implantation metastasis is a common mode of intraperitoneal malignant tumor metastasis. At present, there is still a lack of effective therapeutic means for the treatment of intraperitoneal implantation metastasis. A variety of therapies to control the progression of the disease were tried, including intravenous chemotherapy, abdominal chemotherapy, cytoreductive surgery (CRS), and hyperthermic intraperitoneal chemotherapy (HIPEC). However, these treatments cannot obtain a satisfactory treatment result, due to the scattered metastatic lesions, insufficient penetration depth of intracavity drugs, and insufficient dispersion distribution of drugs, etc. Accordingly, a pressurized nebulizer applied in a medical body cavity was developed.

A conventional pressurized nebulizer applied in the medical body cavity mainly includes a nozzle, an injector and an infusion tube. The injector is configured to pressurize and convey the liquid therein to the nozzle, so that the pressurized liquid is formed into aerosol particles through the nozzle to spray in the body cavity.

However, in the existing pressurized nebulizer, there is a risk of contact contamination to the liquid because the injector needs to be in contact with the liquid; further, there are defects of unstable output aerosol particles and poor control accuracy because the injector works by pumping pressure.

Therefore, there is an urgent need for a pressurized nebulizer which is not limited to the medical field and can solve the above defects.

SUMMARY OF THE INVENTION

An objective of the present invention is to provide a pressurized nebulizer, which avoids contact contamination of liquid, provides a continuous and stable output and has accurate accuracy.

To achieve the above objective, the present invention provides a pressurized nebulizer, including a nozzle, a peristaltic pump, and an elastic braided hose with a maximum pressure endurance value greater than or equal to 2 MPa. The peristaltic pump has a pump head which includes a fixing part, a mating part that is movable relative to the fixing part along an up-down direction of the pump head, a rotating base that is rotatable on the fixing part, and a roller assembled on the rotating base; the rotating base has a circular trajectory when rotating along the rotating base, and the roller is extended beyond the rotating base along a radial direction of the circular trajectory. When the mating part and the fixing part are in a closed state, the elastic braided hose is arranged between the mating part and the fixing part, and jointly between the mating part and the roller; the elastic braided hose includes an input end and an output end located outside the pump head; and the output end of the elastic braided hose is connected with the nozzle. The roller during a rotation with the rotating base has a working stroke of contacting and extruding the elastic braided hose and a non-working stroke of non-contacting with the elastic braided hose; in the working stroke, the roller has a limit position of extruding the elastic braided hose to a limit state, and a movement of the roller in the working stroke is configured to cause liquid coming from the input end of the elastic braided hose to be conveyed to the output end of the elastic braided hose at a pressure greater than or equal to 2 MPa, and then sprayed out at the nozzle; wherein, when the roller is switched to the limit position, a minimum clearance formed between the roller and the mating part is $1.5T \leq P \leq 1.9T$, where T denotes a unilateral wall thickness of the elastic braided hose, and P denotes the minimum clearance.

As a preferable embodiment, the movement of the roller in the working stroke is configured to cause liquid coming from the input end of the elastic braided hose to be conveyed to the output end of the elastic braided hose at a pressure greater than or equal to 2 MPa and less than or equal to 6 Mpa, and the maximum pressure endurance value of the elastic braided hose is greater than or equal to 2 MPa and less than or equal to 8 Mpa.

As a preferable embodiment, the pressurized nebulizer further includes a container for holding the liquid, wherein the input end of the elastic braided hose is connected with the container, and the roller in the working stroke is configured to cause the liquid in the container to be sucked into the elastic braided hose.

As a preferable embodiment, the pressurized nebulizer further includes a Luer taper and a needle connector, wherein the Luer taper is connected with the input end of the elastic braided hose, and one end of the Luer taper away from the input end of the elastic braided hose is connected with the needle connector, and the needle connector is selectively inserted into or pulled out of the container.

As a preferable embodiment, the pressurized nebulizer further includes a guider including a hollow channel, wherein the nozzle is configured to pass through the guider or pull out from the guider along the hollow channel.

As a preferable embodiment, the movement of the roller in the working stroke is configured to cause liquid coming from the input end of the elastic braided hose to be conveyed to the output end of the elastic braided hose at a pressure greater than or equal to 2 MPa and less than or equal to 6 Mpa, and the maximum pressure endurance value of the elastic braided hose is greater than or equal to 2 MPa and less than or equal to 8 Mpa; one or more holding assemblies are provided in the pump head; when two holding assemblies are configured, the two holding assemblies are arranged symmetrically in the pump head for holding two opposite sides of the pump head.

As a preferable embodiment, each holding assembly includes a clamping part arranged on one of the fixing part and the mating part, the clamping part includes a main body and a first elastic arm and a second elastic arm arranged on the main body, the first elastic arm and the second elastic arm together define a clamping channel and an opening for allowing the elastic braided hose to press into or move out of the clamping channel along an up-down direction of the pump head.

As a preferable embodiment, the holding assembly further includes a hold-down part arranged on another of the fixing part and the mating part, the hold-down part is provided with a toothed structure facing the clamping part, the toothed structure is staggered with the clamping part along a left-right direction of the pump head, and the toothed structure is pressed against the elastic braided hose along the up-down direction of the pump head.

As a preferable embodiment, the nozzle includes a nozzle body, a fluid impact pin, an upper thimble, a lower thimble, an inclined thimble, a first elastic component and a second elastic component; the nozzle body is provided with a liquid inlet channel for allowing the liquid from the output end of the elastic braided hose, a lower nozzle hole for ejecting the liquid, an inclined spray channel located beside the liquid inlet channel and laterally communicated with the liquid inlet channel, and an inclined upper nozzle hole connected with the inclined spray channel; the inclined spray channel, the inclined thimble, the second elastic component and the inclined upper nozzle hole together constitute an inclined spray unit, when multiple inclined spray units are configured, the inclined spray units arranged around the liquid inlet channel; the fluid impact pin includes a leg assembled on the nozzle body and a head fixed on the leg, the head is aligned with the lower nozzle hole along an up-down direction of the nozzle body; the upper thimble, the lower thimble and the first elastic component are located in the liquid inlet channel, the first elastic component is further pressed between the upper thimble and the lower thimble, and the first elastic component is configured to always have a tendency to drive the upper thimble to move upward to a first position of cutting the liquid inlet channel from above, and further always have a tendency to drive the lower thimble to move downward to a second position of cutting the liquid inlet channel from underneath; the lower thimble is provided with a connected channel that enables the liquid inlet channel and the lower nozzle hole to be communicated when the lower thimble is in the second position; the second elastic component and the inclined thimble are located in the inclined spray channel, and the second elastic component is configured to always have a tendency to drive the inclined thimble to move upward to a third position of cutting the inclined spray channel from above; and the inclined thimble is provided with an intermediate channel to maintain communication between the inclined spray channel and the inclined nozzle hole when the inclined thimble is in the third position.

As a preferable embodiment, the nozzle body includes a connector, an upper housing, a middle housing and a lower housing, and the connector successively passes through the upper housing and the middle housing and is then threaded with the lower housing, the upper housing and the lower housing are clamped by the connector and the middle housing; a sealing ring is respectively arranged between the connector and the upper housing, between the upper housing and the middle housing, and between the middle housing and the lower housing; the inclined spray channel is formed in the upper housing and the middle housing, the liquid inlet channel is formed in the connector and the lower housing, the lower nozzle hole is formed in the lower housing, the inclined upper nozzle hole is formed in the upper housing, and the output end of the elastic braided hose is connected with the connector.

In comparison with the prior art, the pressurized nebulizer of the invention is configured with a peristaltic pump and an elastic braided hose with a maximum pressure endurance value greater than or equal to 2 MPa, and the minimum clearance P between the roller and the mating part when switching to the limit position is: $1.5T \leq P \leq 1.9T$. Based on the above configurations and the cooperation of the peristaltic pump and the elastic braided hose, the liquid sucked into the elastic braided hose at the input end can be conveyed to the output end of the elastic braided hose at a pressure greater than or equal to 2 MPa, and then sprayed out at the nozzle in forms of aerosol particles. Therefore, the pressure nebulizer of the invention can avoid the contact pollution of the peristaltic pump on the liquid by means of the cooperation of the peristaltic pump and the elastic braided hose, and a continuous and stable output of the aerosol particles from the nozzle may be ensured under the power of the peristaltic pump, thereby achieving accurate accuracy, safety and reliability and convenient operation. In addition, the present invention further overcomes a preconception in the art that "person skilled in the art generally believes that the existing peristaltic pump may only applicable to complex liquid quantitative distribution to achieve high-precision flow transmission control, but not applicable to the pressurization of liquid".

In the existing peristaltic pump, it's ordinarily believed that the peristaltic pump is only applicable to complex liquid quantitative distribution to achieve high-precision flow transmission control. Therefore, the peristaltic pump provided with a pump tube and pump head is generally configured to adapt to this purpose. Usually the pump tube is silicone tube or rubber tube with the maximum pressure withstand value of not exceeding about 5 atmospheric pressures. Further, in order to prevent from damaging the pump tube due to excessive pressure of the liquid in the pump tube exceeding the maximum pressure value, a large clearance is formed between the roller in the existing peristaltic pump and the inner wall of the pump head. It's seen that, the overall structures of the existing peristaltic pump including the material of the pump tube, the maximum pressure value of the pump tube and the clearance of the pump head are designed and configured for the low-pressure quantitative conveying of ordinary liquid. Therefore, it's generally believed in the art that, the existing peristaltic pumps are not applicable to the pressurization of liquid.

Instead, in the pressurized nebulizer of the invention, the peristaltic pump and the elastic braided hose whose maximum pressure withstand value is greater than or equal to 2 MPa are applied, and a minimum clearance P formed between the roller and the mating part is $1.5T \leq P \leq 1.9T$ when the roller is switched to the limit position, thereby achieving high pressure conveying to the nozzle 10 at a pressure greater than or equal to 2 MPa, and there is no contact between the liquid and the peristaltic pump.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

In order to describe the technical content, structural features, achieved objects and effects of the present invention in detail, the following detailed description is given in conjunction with the embodiments and the accompanying drawings.

Figure 1:
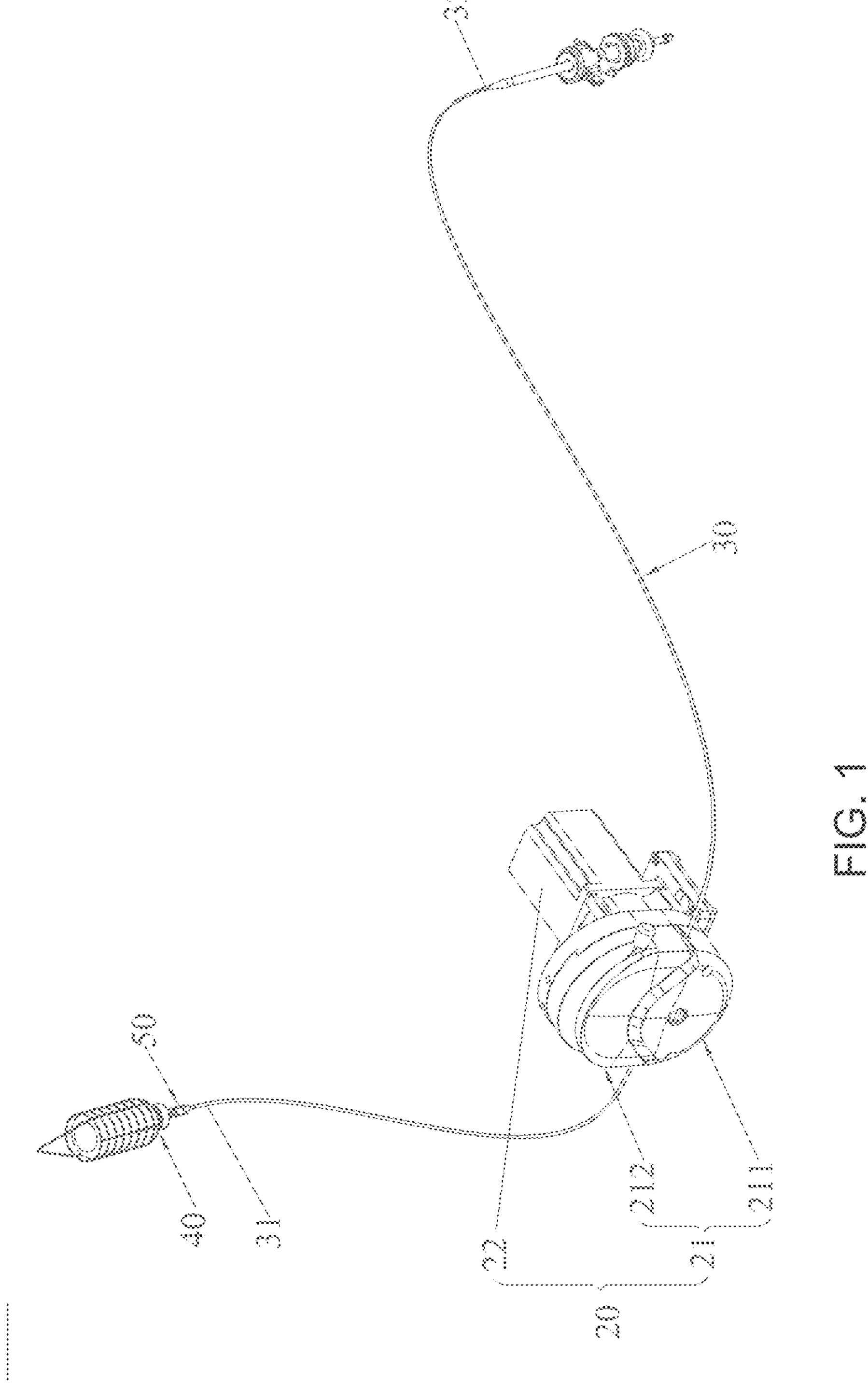
FIG. 1 is a perspective view of a pressure nebulizer according to one embodiment of the invention.
Figure 2:
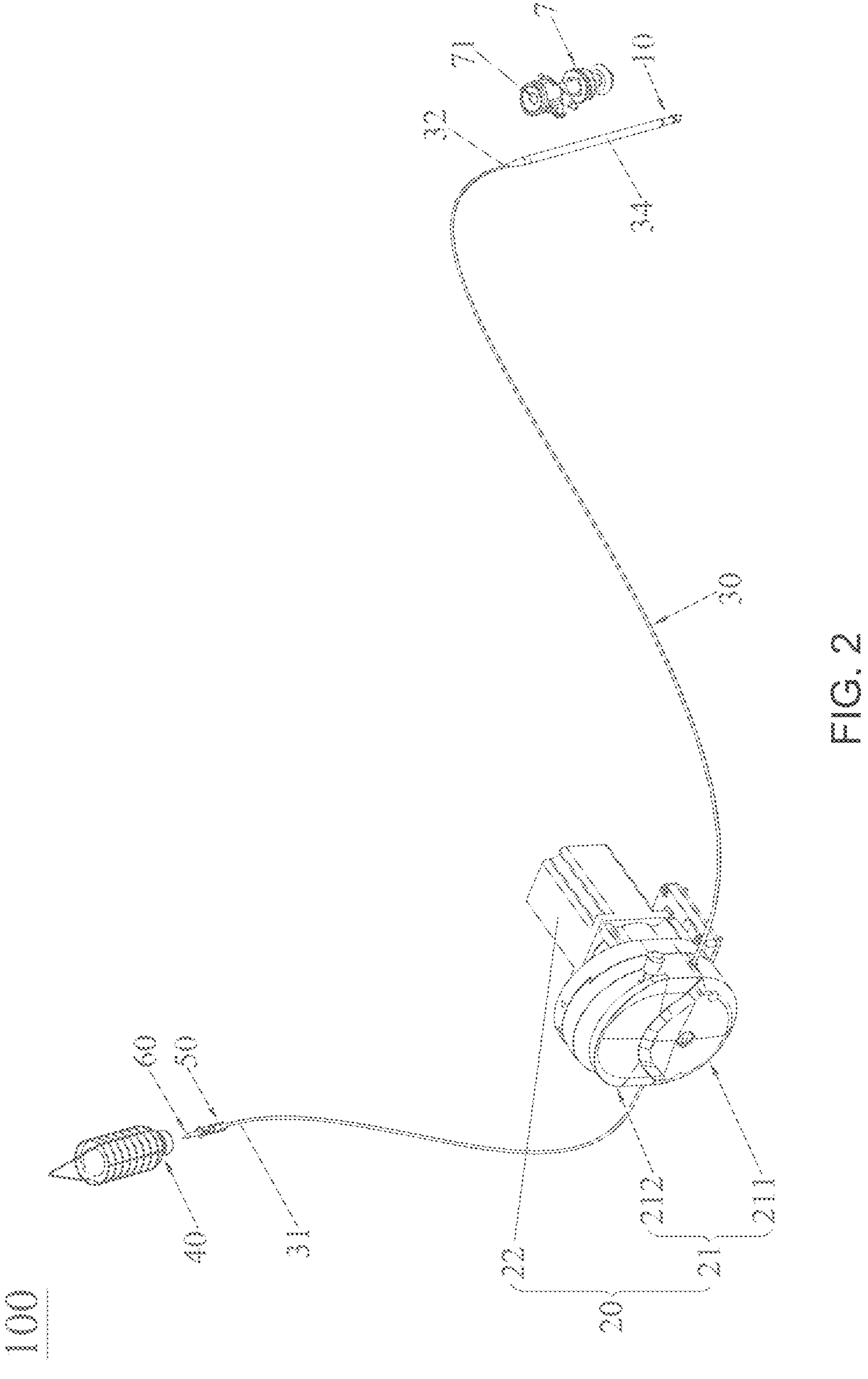
FIG. 2 is an exploded perspective view of the pressurized nebulizer of FIG. 1.
Figure 3:
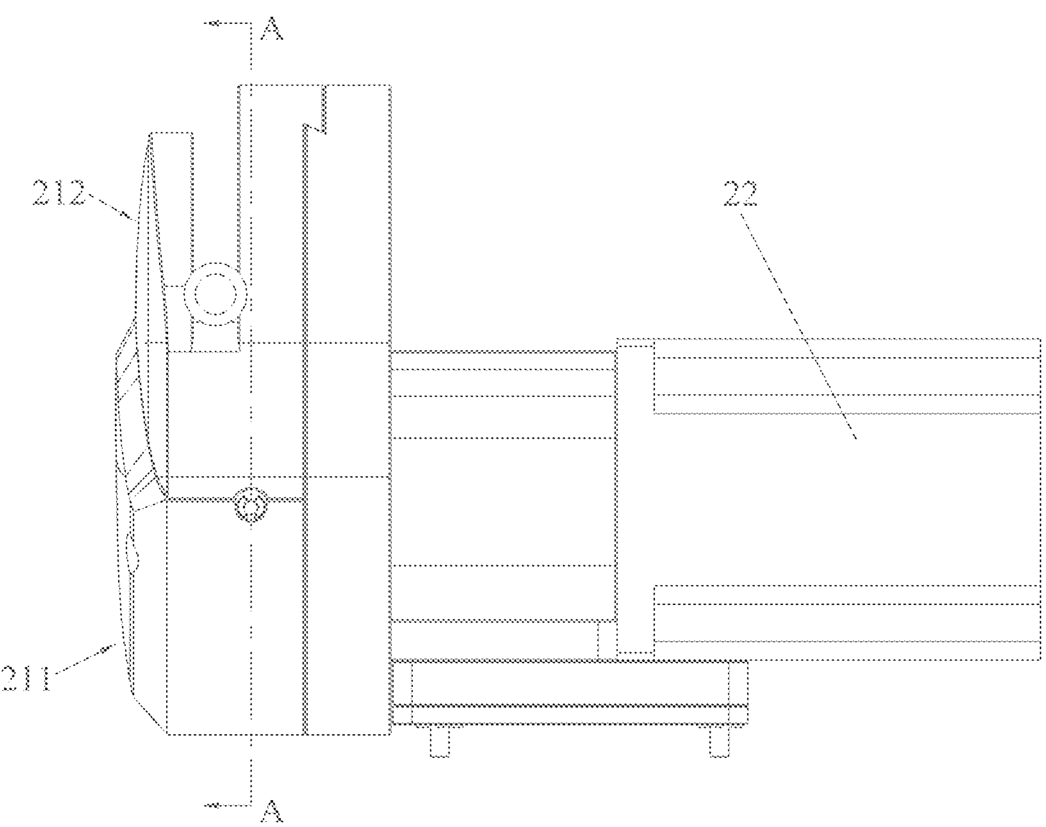
FIG. 3 is a plan view of a peristaltic pump in the pressure nebulizer showing the mating part and the fixing part are in a closed status, and also showing part of the elastic braided hose.
Figure 4:
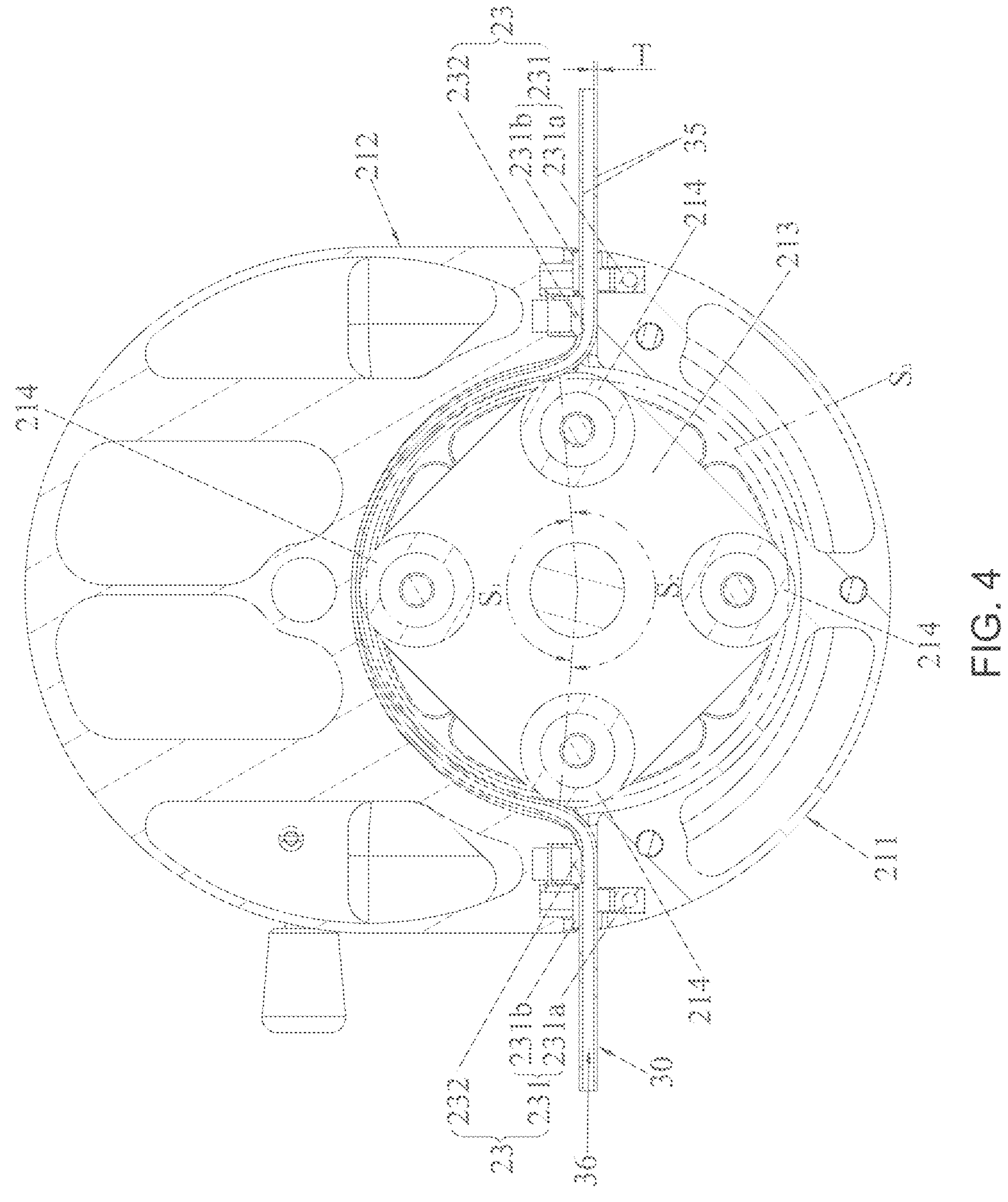
FIG. 4 is a cross section view cut along the A-A line in FIG. 3.

Referring to FIGS. 1, 2, 4 and 5, the pressurized nebulizer 100 according to the present invention includes a nozzle 10, a peristaltic pump 20, an elastic braided hose 30, a container 40, a Luer taper 50, a needle connector 60 and a guider 70. The peristaltic pump 20 has a pump head 21 including a fixing part 211, a mating part 212 that is movable relative to the fixing part 211 along an up-down direction of the pump head 20, a rotating base 213 that is rotatable on the fixing part 211, and a roller 214 assembled on the rotating base 213. When rotating along the rotating base 213, the roller 214 has a circular trajectory (referring to the circle denoted by $S_3$ in FIG. 4), and the roller 214 is extended beyond the rotating base 213 along a radial direction of the circular trajectory, so that the roller 214 during the rotation with the rotating base 213 may provide a working stroke $S_1$ and a non-working stroke $S_2$ as described below. When the mating part 212 and the fixing part 211 are in a closed state, as shown in FIGS. 1, 2 and 4, the elastic braided hose 30 is arranged between the mating part 212 and the fixing part 211, and jointly between the mating part 212 and the roller 214. The elastic braided hose 30 includes an input end 31 and an output end 32. One end of the Luer taper 50 is connected with the input end 31 of the elastic braided hose 30, and another end of the Luer taper 50 is connected with the needle connector 60, that is, the input end 31 of the elastic braided hose 30 and the needle connector 60 are respectively arranged on opposite sides of the Luer taper 50. The needle connector 60 may be selectively inserted into or pulled out of the container 40, in such a way, the operation of connecting or disconnecting the elastic braided hose 30 with the container 40 is simple and convenient. Optionally, as an embodiment in FIGS. 1 and 2, the container 40 is a bottle, or may be in other forms for containing liquid, which is not limited to that shown in FIGS. 1 and 2.

As illustrated, the output end 32 of the elastic braided hose 30 is connected to the nozzle 10, and the nozzle 10 may pass through the guider 70 or pull out from the guider 70 along its hollow channel 71 of the guider 70. Optionally, the guider 70 may be a puncture device as shown in FIG. 1 and FIG. 2, or may be a drainage tube according to actual needs. When the pressurized nebulizer 100 of the invention is applied to medical purposes, the nozzle 10 may enter the abdominal cavity of the human body more smoothly and reliably with the cooperation of the guider 70, for delivering drug to the abdominal cavity. In addition, in order to facilitate the nozzle 10 to pass through or pull out from the hollow channel 71 of the guider 70, the output end 32 of the elastic braided hose 30 is covered with a rod 34 which is also connected with the nozzle 10, specifically with the connector 11*a* described below.

Furthermore, the roller 214 in the process of rotating with the rotating base 213 has a working stroke $S_1$ of contacting and extruding the elastic braided hose 30 from underneath and a non-working stroke $S_2$ of non-contacting with the elastic braided hose 30. Specifically, in the working stroke $S_1$, the roller 214 contacts with the elastic braided hose 30 at the beginning, and gradually extrudes the elastic braided hose 30 until the elastic braided hose 30 deforms to the limit state, and then, the elastic braided hose 30 gradually recovers from the limit state to the state just contacting with the roller 214; while in the non-working stroke $S_2$, the roller 214 is not in contact with the elastic braided hose 30, thereby realizing one peristaltic cycle of the peristaltic pump 20. Further, in the working stroke $S_1$, the roller 214 has a limit position of extruding the elastic braided hose 30 to the limit state, as shown in FIG. 4. In the working stroke $S_1$, the roller 214 is configured to cause the liquid coming from the output end to be conveyed to the output end of the elastic braided hose at a pressure greater than or equal to 2 MPa, preferably at a pressure greater than or equal to 2 MPa and less than or equal to 6 Mpa, and then the liquid is sprayed out from the nozzle 10. In such a way, the pressurized nebulizer 100 of the invention realizes the purpose of atomizing the liquid into aerosol particles.

Specifically, when the roller 214 is switched to the limit position, the minimum clearance P formed between the roller 214 and the mating part 212 is $1.5T \leq P \leq 1.9T$, where T denotes a unilateral wall thickness (namely the outer diameter minus the inner diameter, and divided by two) of the elastic braided hose. In such an arrangement, when the roller 214 is switched to the limit position, the internal clearance 36 of the elastic braided hose 30 is squeezed to zero, and then the tube wall 35 of the elastic braided hose 30 is further compressed and deformed with a compression deformation being greater than or equal to 0.1T and less than or equal to 0.5T, thus ensuring the reliability of the peristaltic pump 20 to transfer the liquid in the elastic braided hose 30 from the output end 32 of the elastic braided hose 30 to the nozzle 10 at a pressure greater than or equal to 2 MPa and less than or equal to 6 MPa. It should be noted that in the working stroke $S_1$, the liquid in the container 40 is sucked into the elastic braided hose 30 under the movement of the roller 214. The input end 31 of the elastic braided hose 30 is connected to the container 40 through the needle connector 60 and the Luer taper 50. It's understood that, the input end 31 of the elastic braided hose 30 may be directly connected to the container 40 when no Luer taper 50 and no needle connector 60 is used. In addition, the guider 70 may be deleted as needed.

Figure 5:
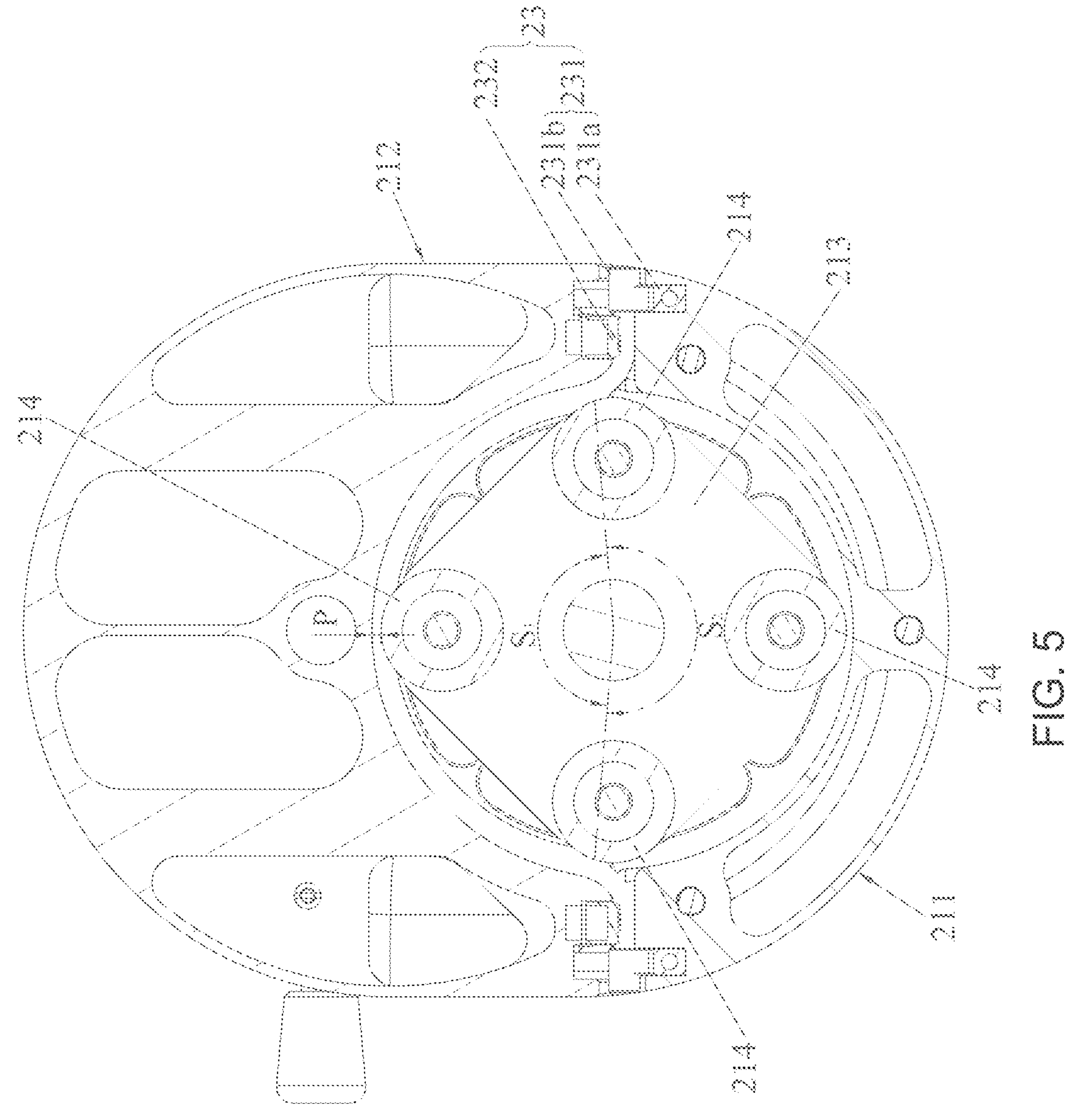
FIG. 5 is a partial view of FIG. 4 with the elastic braided hose being hidden.
Figure 6:
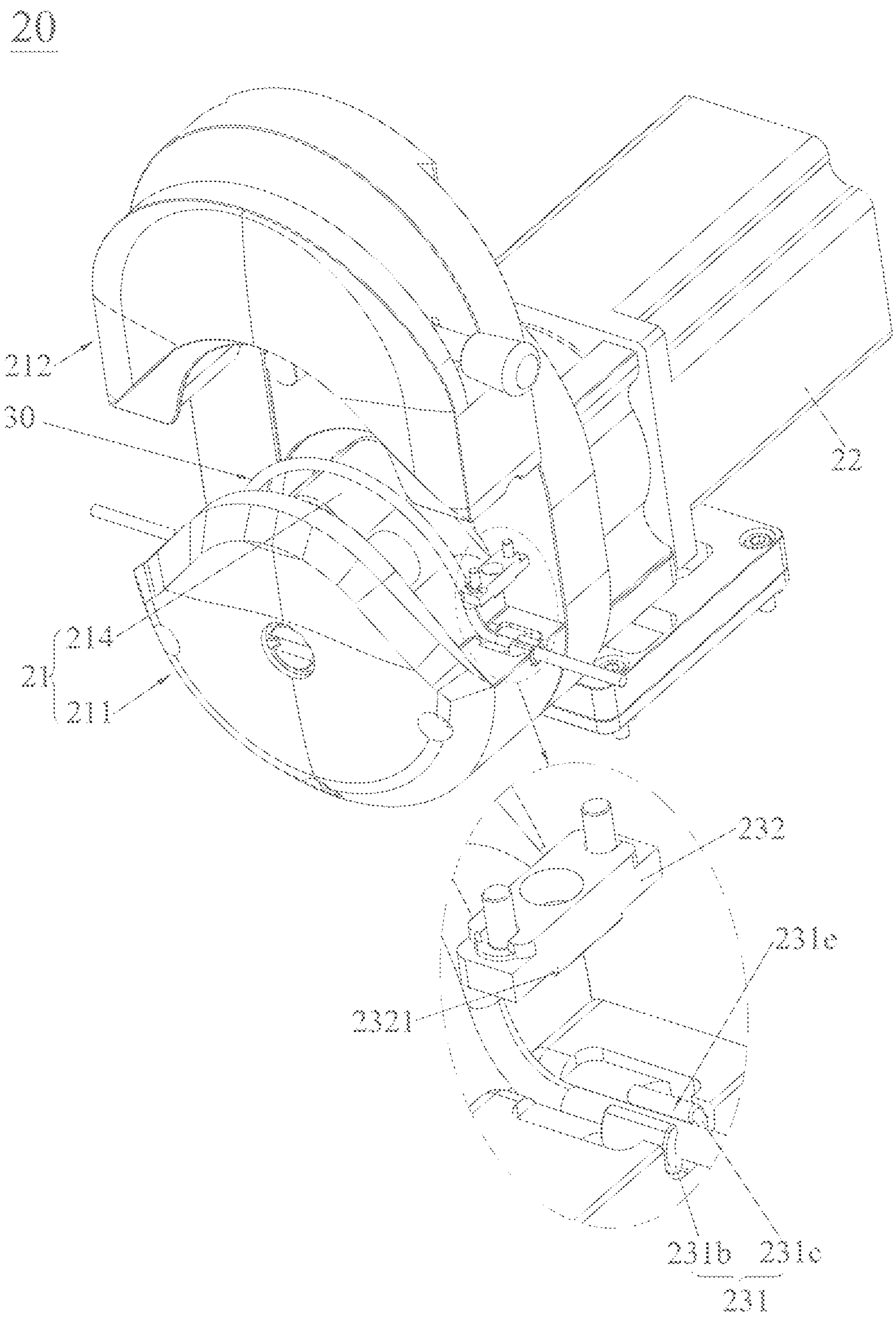
FIG. 6 is an exploded view of the peristaltic pump in the pressurized nebulizer according to one embodiment of the invention.
Figure 7:
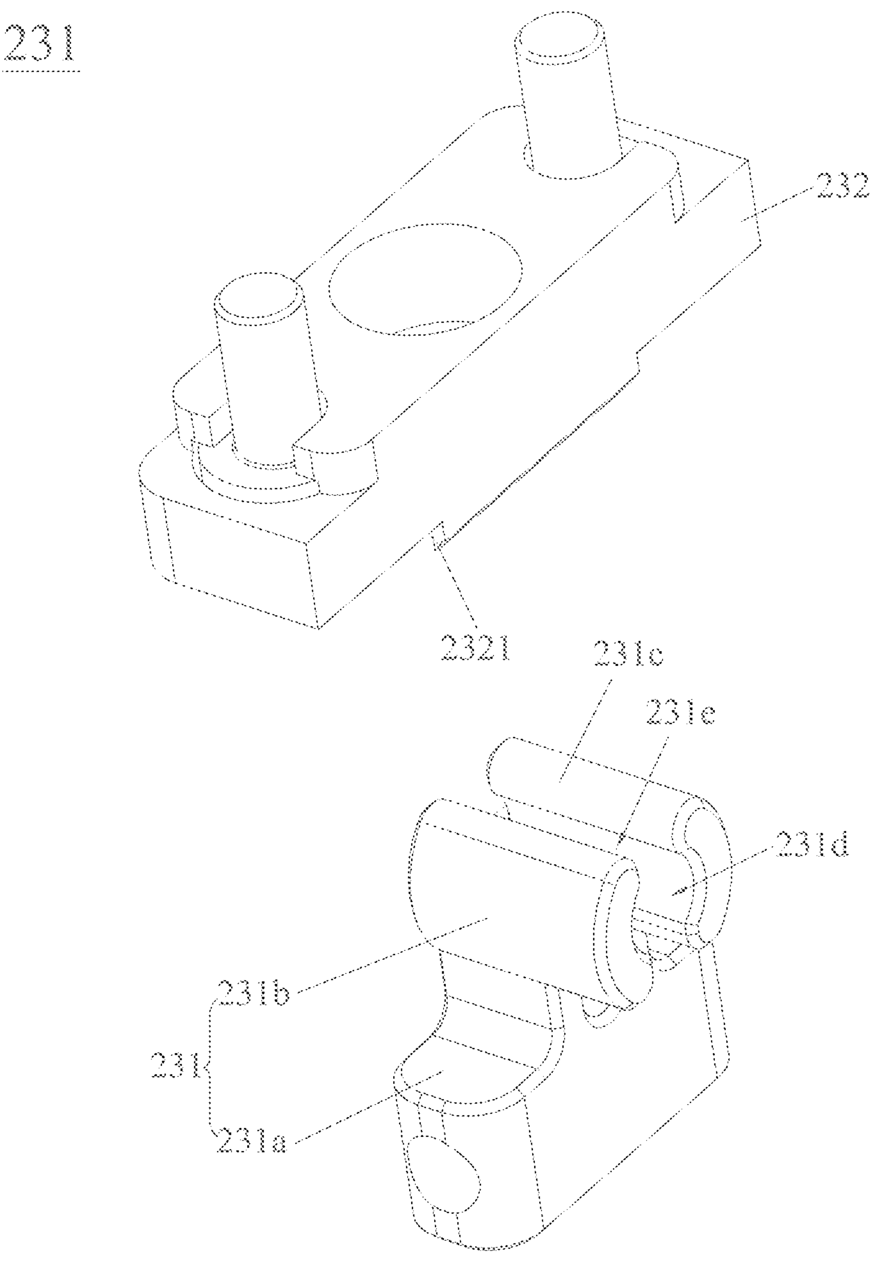
FIG. 7 is a perspective view of the holding assembly of the peristaltic pump in the pressurized nebulizer of the invention when separated.
Figure 8:
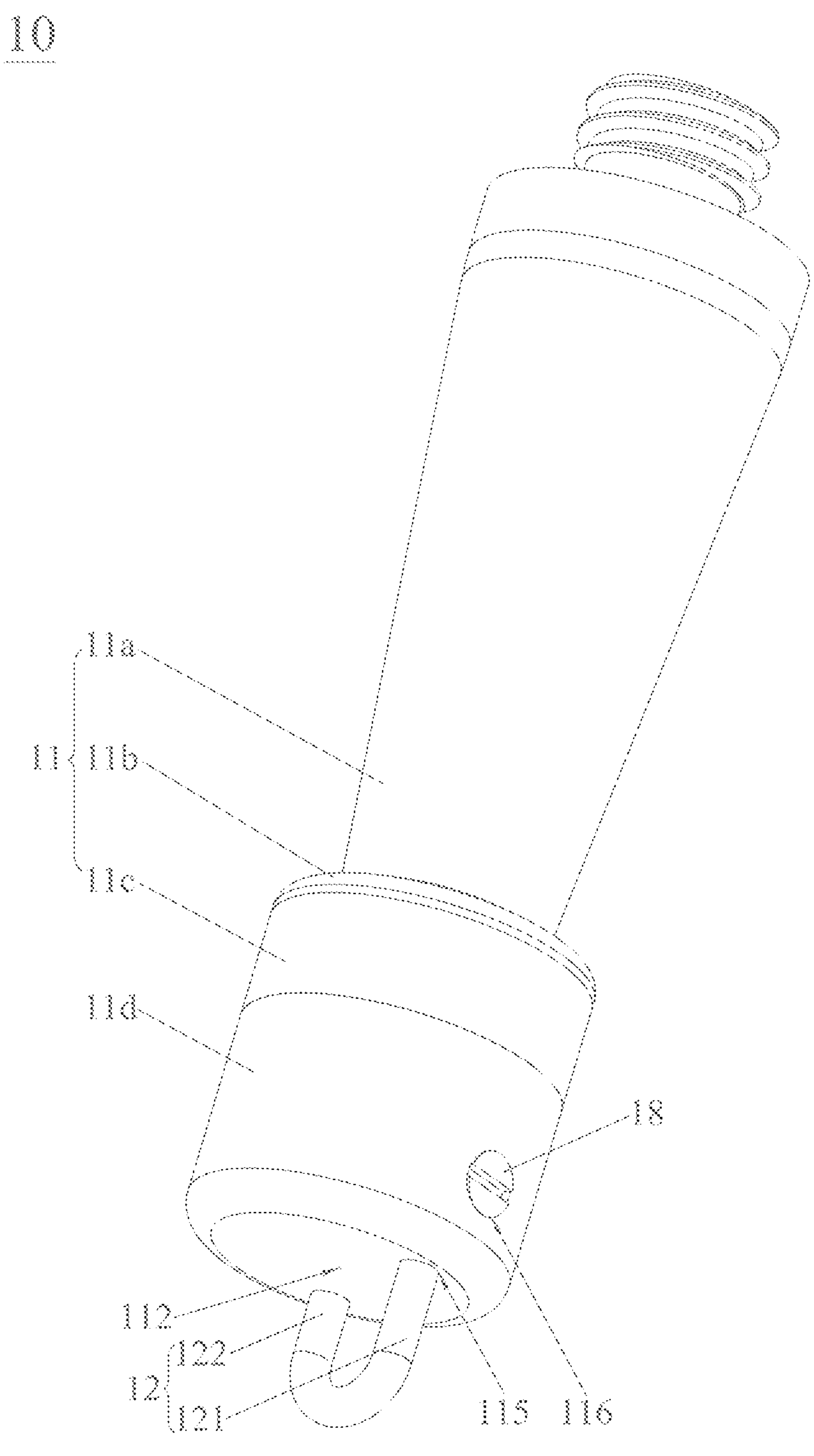
FIG. 8 is a perspective view of the nozzle of the pressurized nebulizer according to one embodiment of the invention.

As shown in FIG. 4 to FIG. 5, in order to reduce the unstable movement of elastic braided hose 30 during the ejection of high pressure liquid, two holding assemblies 23 are provided in the pump head 21 for stabilizing. Specifically, the two holding assemblies 23 are arranged symmetrically on the pump head 21, so as to firmly hold the elastic braided hose 30 at two opposite sides of the pump head 21, which avoids unstable movement in the working stroke $S_1$ of the roller 214, thus ensuring the reliability of the pressurized nebulizer 100 of the invention. Specifically, in conjunction with FIG. 6 to FIG. 7, as an embodiment, the holding assembly 23 includes a clamping part 231 arranged on the fixing part 211 and a hold-down part 232 arranged on the mating part 212. Optionally, the arranging positions of the clamping part 231 and the hold-down part 232 may be switched according to actual needs. Specifically, the clamping part 231 includes a main body 231*a*, and a first elastic arm 231*b* and a second elastic arm 231*c* arranged on the main body 231*a*. The first elastic arm 231*b* and the second elastic arm 231*c* together define a clamping channel 231*e* and an opening 231*d* for allowing the elastic braided hose 30 to press into or move out of the clamping channel 231*e* along the up-down direction of the pump head 21. Based on the above configurations, the elastic braided hose 30 may be installed into the clamping channel 231*e* by stretching the opening 231*d*, so that the elastic braided hose 30 can be clamped and held between the first elastic arm 231*b* and the second elastic arm 231*c* with their respective reset elasticity. Meanwhile, the hold-down part 232 is provided with a toothed structure 2321 facing the clamping part 231, the toothed structure 2321 is staggered with the clamping part 231 along the left-right direction of the pump head 21, and is further pressed against the elastic braided hose 30 along the up-down direction of the pump head 21. Based on theses configurations, the elastic braided hose 30 is not only held tightly by the first elastic arm 231*b* and the second elastic arm 231*c*, but also jointly held by the toothed structure 2321 and the fixing part 211. Therefore, the elastic braided hose 30 may be more reliably stabilized when the mating part 212 and the fixing part 211 are in the close state.

Referring to FIGS. 8-11, the nozzle 10 includes a nozzle body 11, a fluid impact pin 12, upper thimble 13, lower thimble 14, inclined thimble 15, first elastic component 16, and second elastic component 17. The nozzle body 11 is provided with a liquid inlet channel 111 for allowing the liquid from the output end 32 of the elastic braided hose 30, a lower nozzle hole 112 for ejecting the liquid, an inclined spray channel 113 located beside the liquid inlet channel 111 and laterally communicated with the liquid inlet channel 111, and an inclined upper nozzle hole 114 connected with the inclined spray channel 113. Alternatively, in FIG. 13 and FIG. 14, as an embodiment, the center lines of the liquid inlet channel 111 and lower nozzle hole 112 coincide (as indicated by C1 in FIG. 14), and the center lines of inclined spray channel 113 and inclined upper nozzle hole 114 coincide (as indicated by C2 in FIG. 14), and an angle α between the center line of the liquid inlet channel 111 and the center line of the inclined spray channel 113 is from 15 to 30 degrees, for example, 15 degrees, 17 degrees, 19 degrees, 21 degrees, 23 degrees, 25 degrees, 27 degrees or 30 degrees. With the help of the inclined upper nozzle holes 114, the spray range of the nozzle 10 may be further increased. Optionally, the angle α between the center line of the liquid inlet channel 111 and the center line of the inclined spray channel 113 may be set at other degrees, which is not limited as FIG. 14.

Specifically, the fluid impact pin 12 includes a leg 121 assembled on the nozzle body 11 and a head 122 fixed on the leg 121, the head 122 is aligned with the lower nozzle hole 112 along the up-down direction of the nozzle body 11, so as to ensure that the high-speed and high-pressure jet flow jetted from the lower nozzle hole 112 is vertically impacted on the head 122, for example, on the end face 1221 of the head 122. As a result, the jet flow is dispersed accordingly, toward to all directions as shown the arrows near the end face 1221 in FIGS. 12, so that the spray angle of the nozzle 10 can be broadened. Alternatively, as an embodiment, in FIGS. 8, 9, 11 and 12, the upper end of fluid impact pin 12 is assembled and fixed on the nozzle body 11, and the lower end of the fluid impact rod 121 is extended down the nozzle body 11, and the lower end of the fluid impact pin 12 is bended upward to form the head 122, so that the fluid impact pin 12 is in a "J" shape. Optionally, the fluid impact pin 12 may be in other shapes, which is not limited to that shown in FIGS. 8, 9, 11 and 12.

Figure 13:
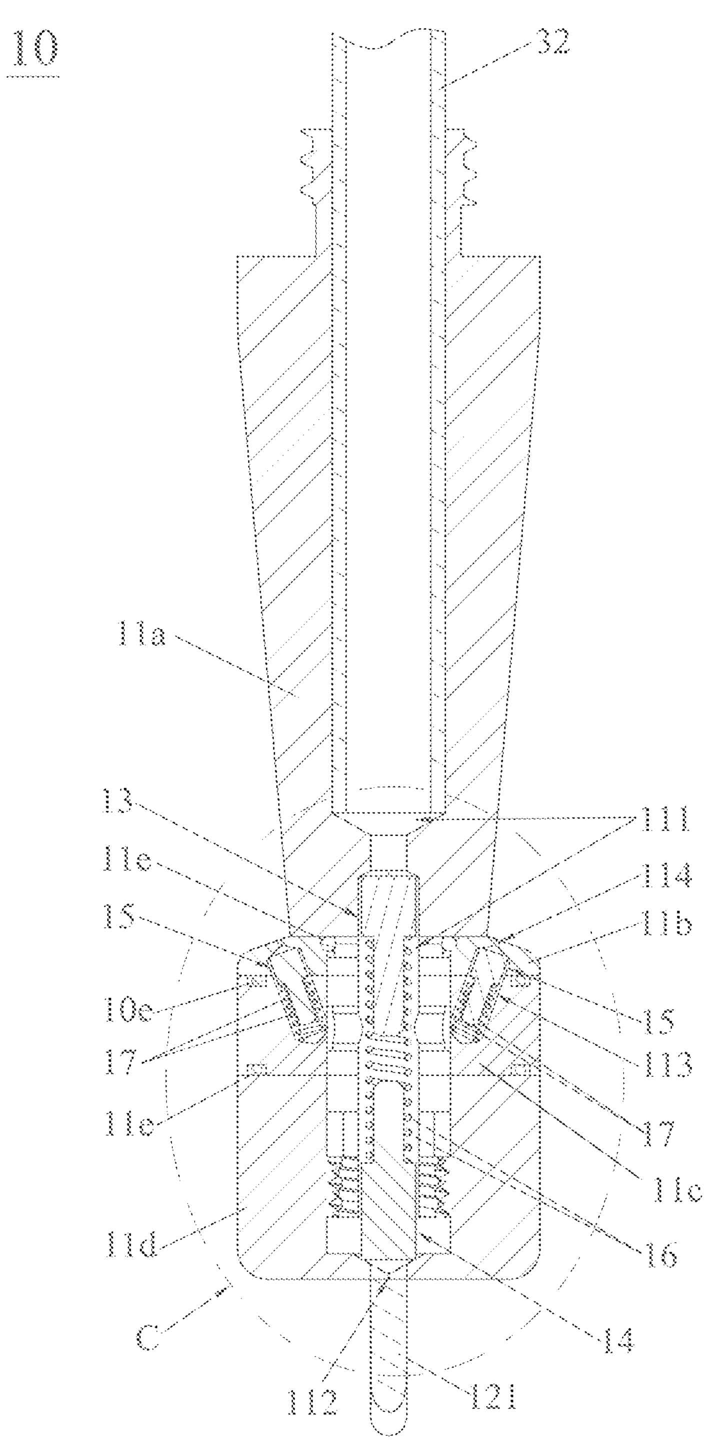
FIG. 13 is a cross section view cut along the B-B line in FIG. 12.
Figure 14:
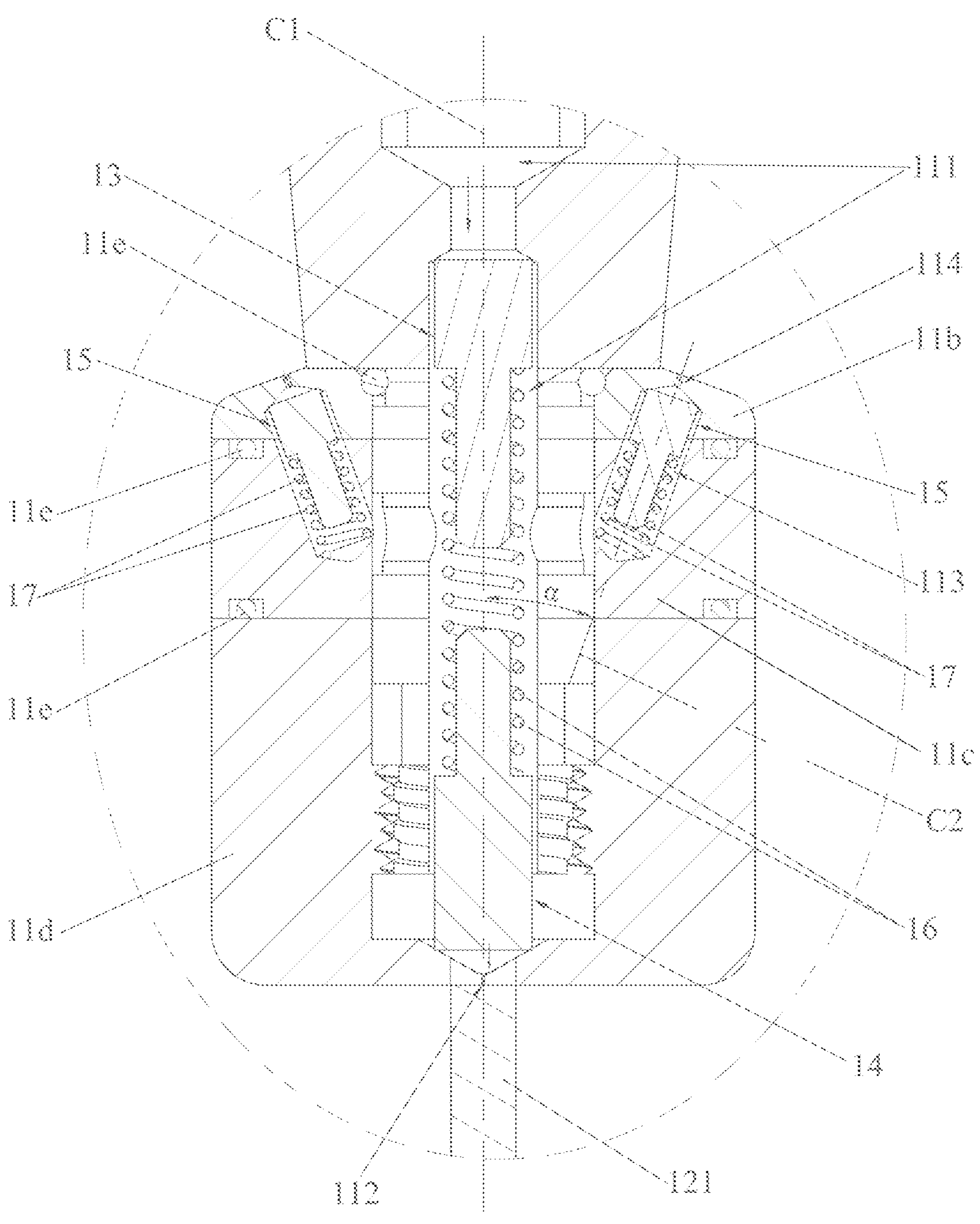
FIG. 14 is an enlarged view of Part C of FIG. 13.
Figure 15:
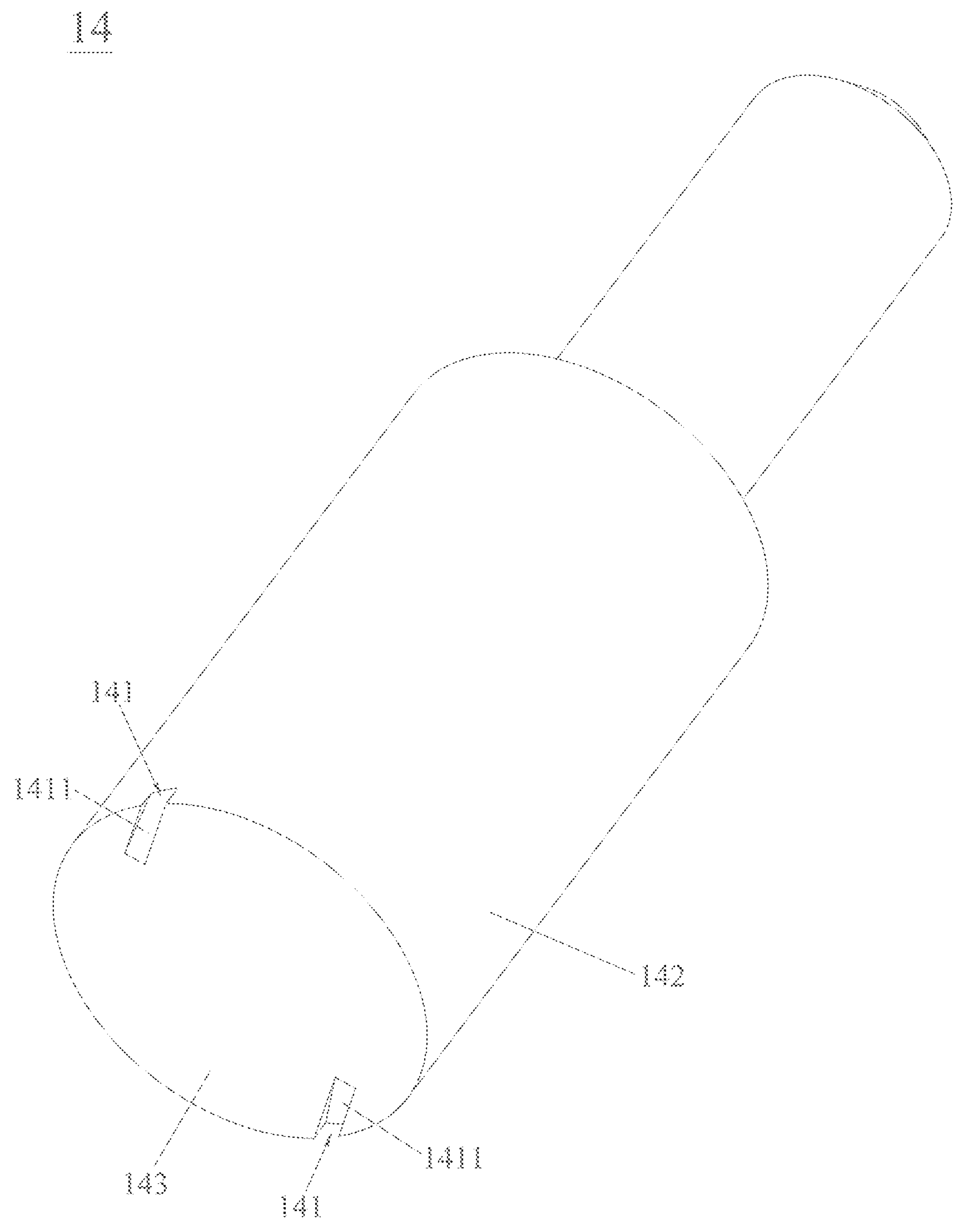
FIG. 15 is a perspective view of the thimble of the nozzle in the pressurized nebulizer of the invention.

As shown in FIGS. 13-15, the upper thimble 13, the lower thimble 14 and the first elastic component 16 are located and received in the liquid inlet channel 111, which makes the appearance of the nozzle 10 concise. The first elastic component 16 is further pressed between the upper thimble 13 and the lower thimble 14, and the first elastic component 16 is configured to always have a tendency to drive the upper thimble 13 to move upward to a first position of blocking the liquid inlet channel 111 from above, that is, when the upper thimble 13 is in the first position, the fluid inlet channel 111 is cut off by the upper thimble 13 from above. Further, the first elastic component 16 is configured to always have a tendency to drive the lower thimble 14 to move downward to a second position of blocking the liquid inlet channel 11 from underneath, as shown in FIG. 13 and FIG. 14. In combination with FIG. 15, the lower thimble 14 is provided with a connected channel 141 that enables the liquid inlet channel 111 and the lower nozzle hole 112 to be communicated when the lower thimble 14 is in the second position, so that the liquid in the liquid inlet channel 111 can be jetted from the lower nozzle hole 112. The second elastic component 17 and the inclined thimble 15 are located in the inclined spray channel 113, and namely received in the nozzle body 11, which makes the appearance of the nozzle 10 concise. The second elastic component 17 is configured to always have a tendency to drive the inclined thimble 15 to move upward to a third position of the inclined spray channel 113 from above. That is, when the inclined thimble 15 is in the third position, the inclined spray channel 113 is cut off by the inclined thimble 15 from above, as shown in FIGS. 13 and 14. In combination with FIG. 16, an intermediate channel 151 is provided on the inclined thimble 15 to maintain communication between the inclined spray channel 113 and the inclined nozzle hole 114 when the inclined thimble 15 is in the third position, so that the liquid in the liquid inlet channel 111 may pass through the inclined spray channel 113 and then jet out from the inclined nozzle hole 114. In such a way, the spray range of the nozzle 10 may be further broadened. In addition, more detailed structure of the nozzle 10 follows.

Figure 9:
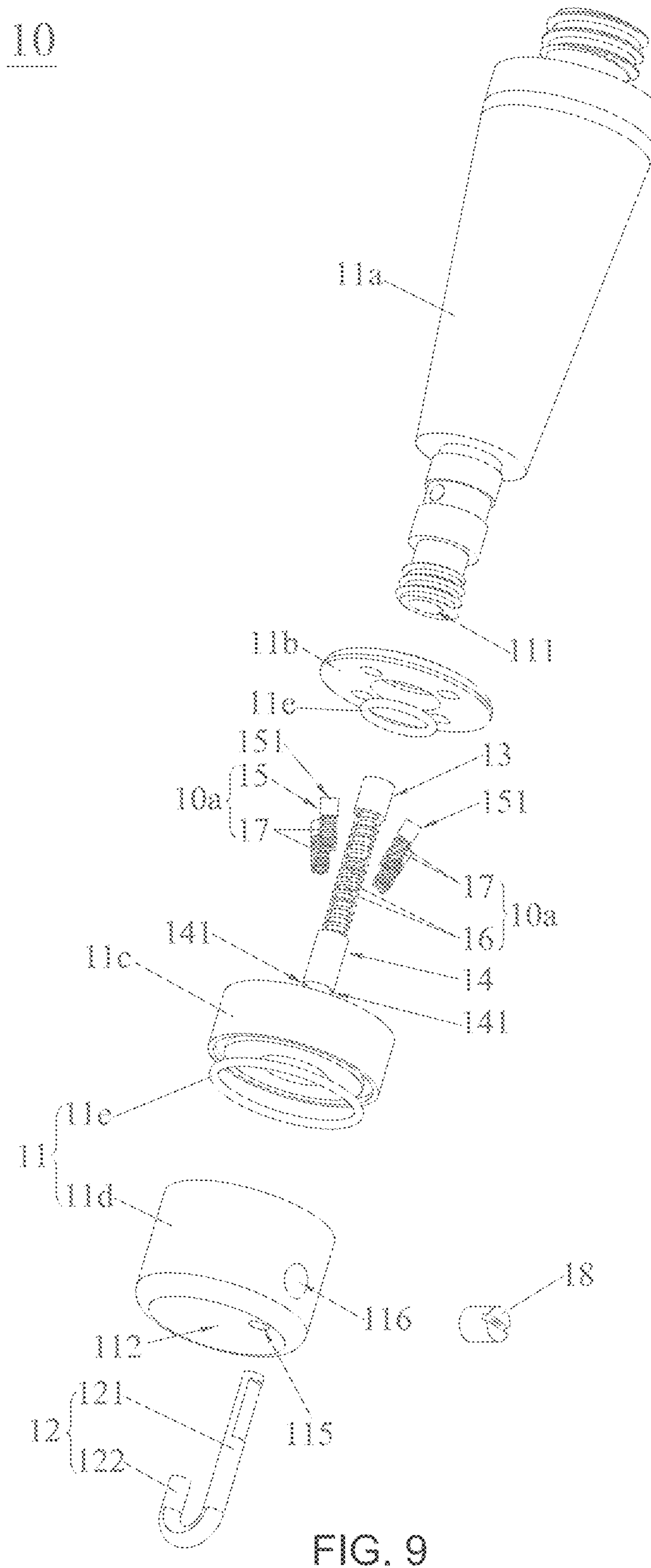
FIG. 9 is an exploded view of FIG. 8.
Figure 10:
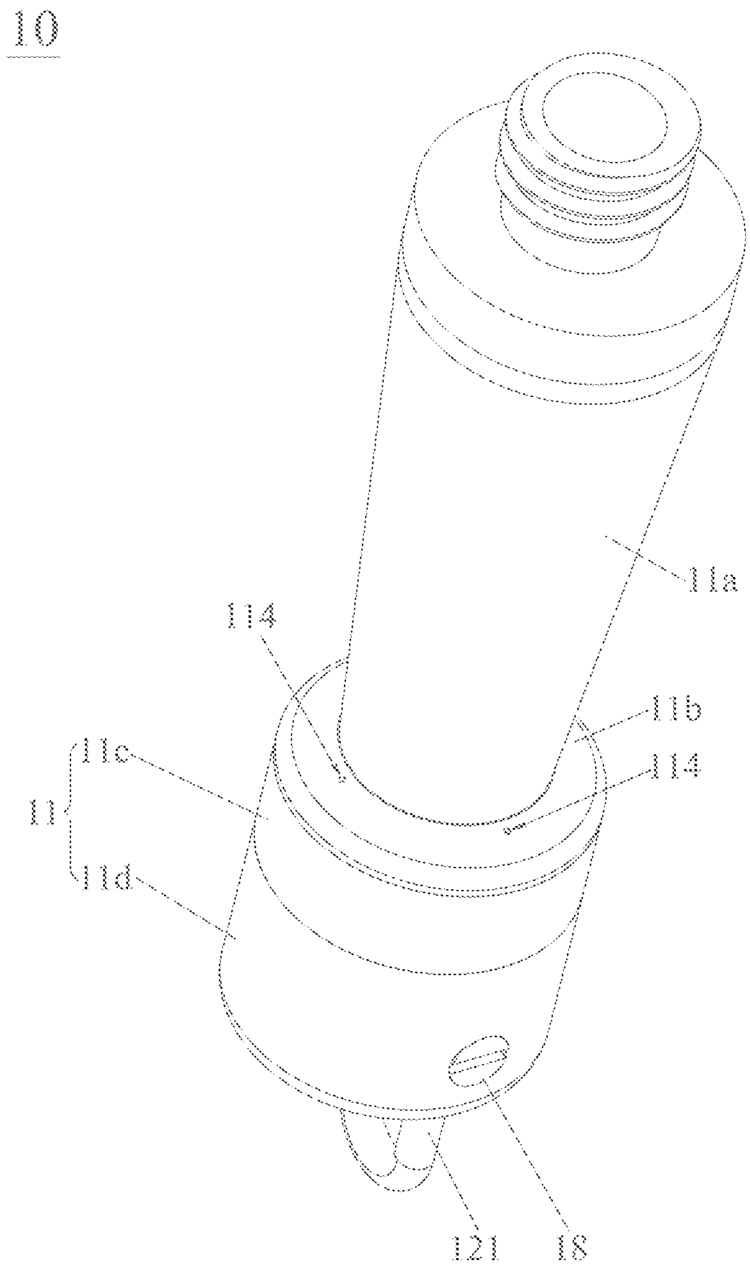
FIG. 10 is another perspective view of the nozzle of FIG. 8.
Figure 11:
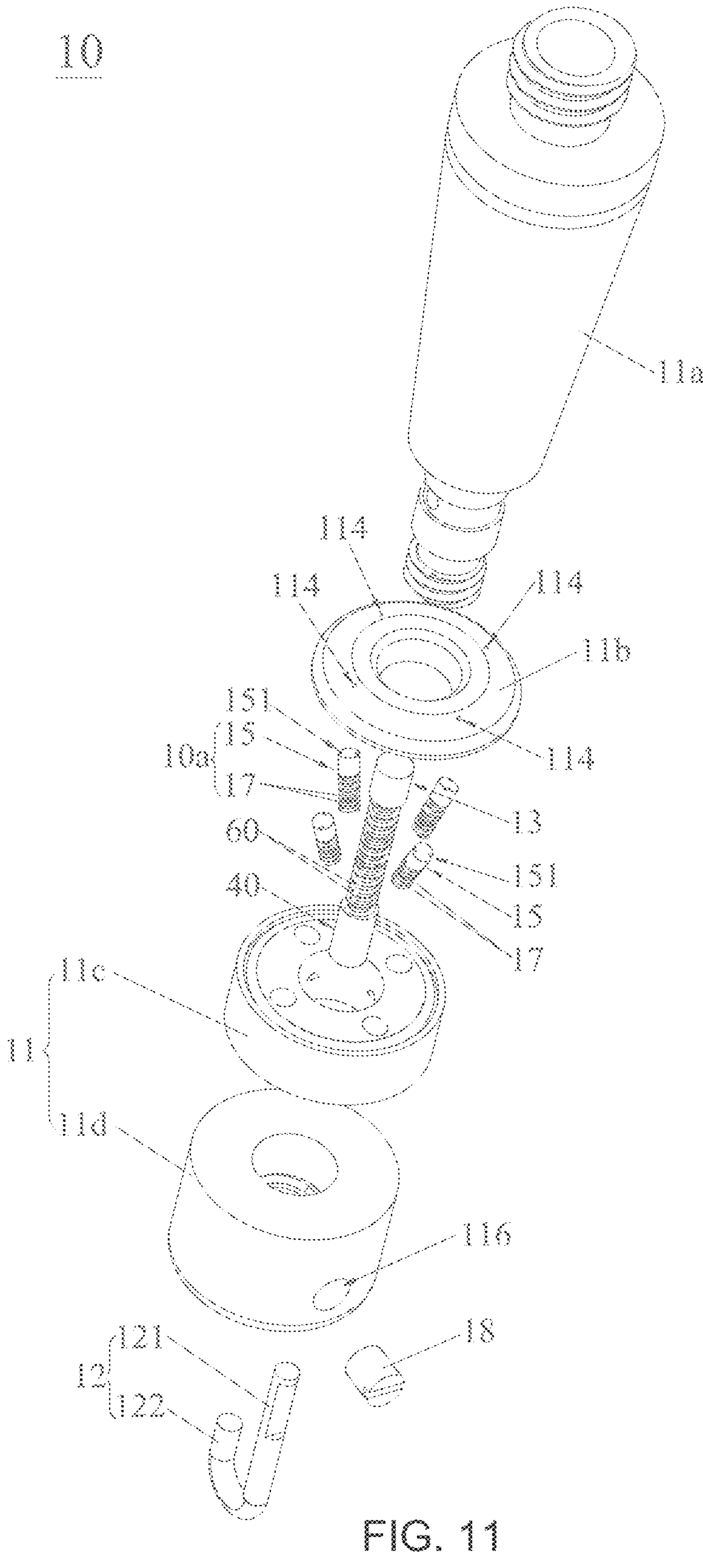
FIG. 11 is an exploded view of FIG. 10.
Figure 12:
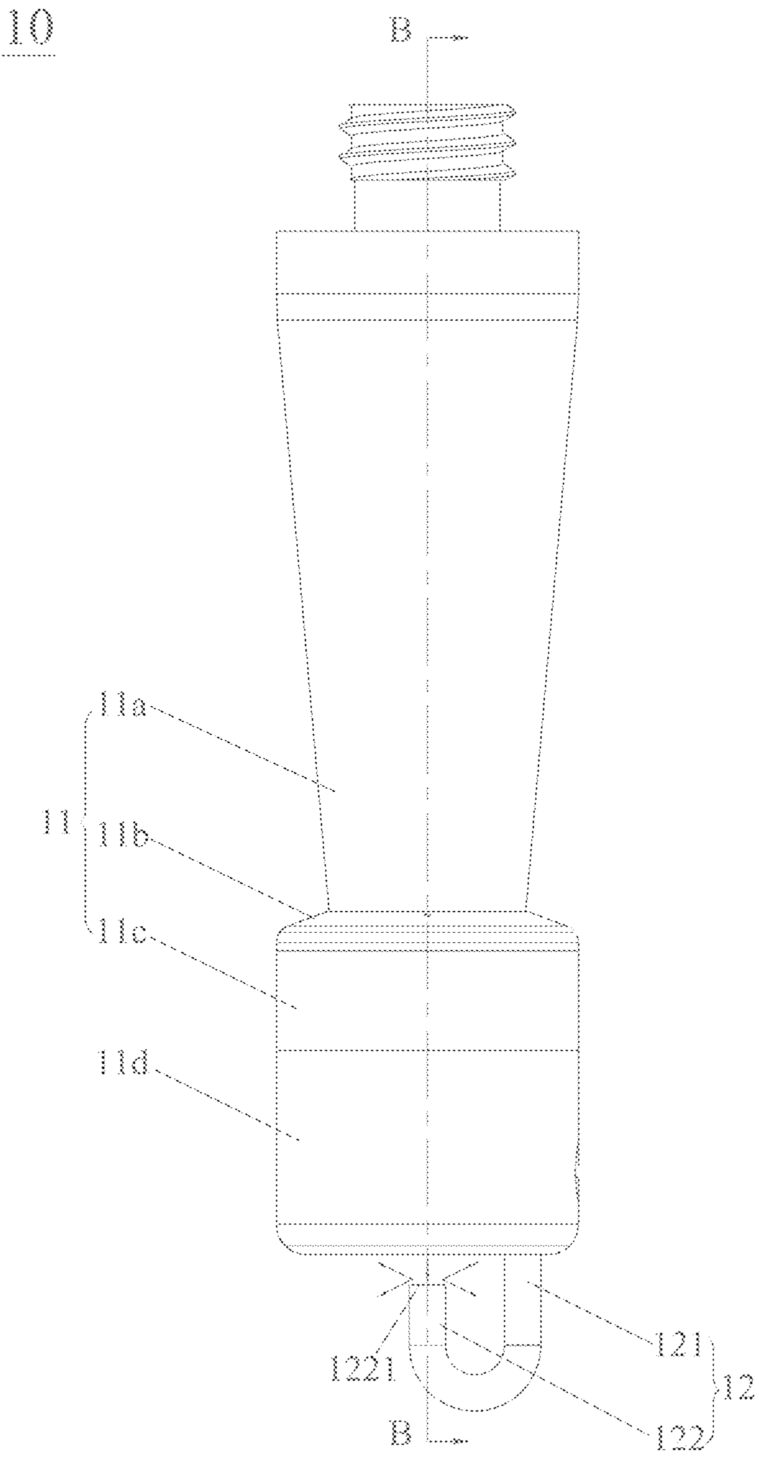
FIG. 12 is a plan view of FIG. 8.

As shown in FIG. 9 and FIG. 11, the inclined spray channel 113, the inclined thimble 15, the second elastic component 17 and the inclined upper nozzle hole 114 together constitute an inclined spray unit 10*a*. Preferably, four inclined spray units 10*a* are configured and arranged around the liquid inlet channel 111, thereby further increasing the spray range of the nozzle 10. Optionally, the inclined spray units 10*a* with other quantities may be configured according to the actual needs, which is not limited to that shown in FIGS. 9 and 11. Specifically, in FIG. 9 and FIG. 11, as an embodiment, the first elastic component 16 and the second elastic component 17 are compression springs to simplify the structure. In other embodiments, the first elastic component 16 and the second elastic component 17 may be tensile springs, which is not limited specifically. In addition, the length of the first elastic component 16 is greater than the length of the second elastic component 17. Preferably, as an embodiment in FIGS. 9 and 11, the length of the first elastic component 16 is greater than twice the length of the second elastic component 17 and less than three times the length of the second elastic component 17, which facilitates the first elastic component 16 to simultaneously drive the upper thimble 13 to the first position and drive the lower thimble 14 to the second position. Optionally, the length of the first elastic component 16 may be greater than three times the length of the second elastic component 17 according to actual needs. In addition, each of the upper thimble 13, the lower thimble 14 and the inclined thimble 15 is in a form of cylinder to facilitate the manufacturing, which is not limited to this however.

Figure 16:
FIG. 16 is a perspective view of the inclined thimble of the nozzle in the pressurized nebulizer of the invention.
Figure 16:
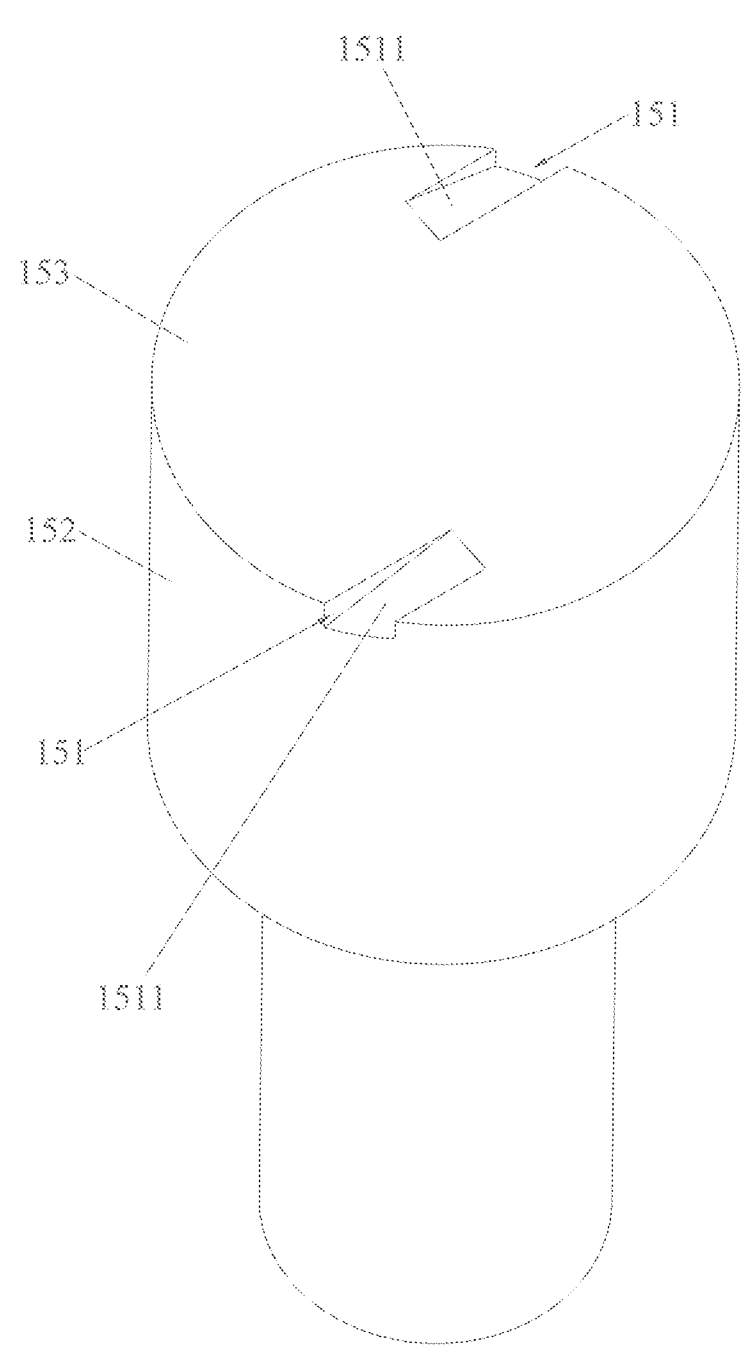

As shown in FIG. 16, two intermediate channels 151 are arranged in center symmetry on the inclined thimble 15, so as to increase connections between the inclined spray channel 113 and the inclined upper nozzle hole 114, thereby further improving spray effect. Optionally, the intermediate channels 151 with other quantities may be configured according to actual demands, which is not limited to that in FIG. 16. As an embodiment, the intermediate channels 151 is a first notch structure that runs through a side surface 152 and a top surface 153 of the inclined thimble 15, and a bottom wall 1511 of the first notch structure is defined with a first inclined plane which is inclined upward from the side surface 152 of the inclined thimble 15 to the top surface 153 of the inclined thimble 15. In such a way, the liquid in the inclined spray channel 113 can be pressurized and accelerated by the middle channel 151 when passing, to make the aerosol particles sprayed from the inclined upper nozzle hole 114 smaller. It should be noted that the aforementioned center symmetry means that any of the intermediate channels can overlap with one of the others after rotated around the center line of the inclined thimble 15.

As shown in FIG. 15, two connected channels 141 are arranged in a center symmetry on the lower thimble 14, to increase the connections between the liquid inlet channel 111 and the lower nozzle hole 112, thereby further improving the spray effect. Optionally, the connected channels 141 with other quantities may be configured according to actual demands, which is not limited to that in FIG. 15. As an embodiment, the connected channels 141 is a second notch structure that runs through a side surface 142 and a bottom surface 143 of the lower thimble 14, and a top wall 1411 of the notch structure is defined with a second inclined plane which is inclined upward from the side surface 132 of the lower thimble 14 to the bottom surface 143 of the lower thimble 14. In such a way, the liquid in the connected channels 141 can be pressurized and accelerated by the connected channels 141 when passing, so that the jet flow sprayed by the lower nozzle hole 112 can hit the end face of the head 122 at a higher speed and higher pressure, thereby obtaining smaller liquid particles to improving the atomization effect. It should be noted that the aforementioned center symmetry means that any of the connected channels 114 can overlap with one of the others after rotated around the center line of the lower thimble 14.

As shown in FIG. 8 to FIG. 11, the nozzle 10 also includes a locking screw 18, the nozzle body 11 is provided with an installation channel 115 extending up and down and a side threaded hole 116 connected with the installation channel 115, and the locking screw 18 is screwed into the side thread hole 116 to lock the upper end of the leg 121. Based on the cooperation of the side thread hole 116 and the locking screw 18, the assembly and disassembly of the fluid impact pin 12 on the nozzle body 11 is more convenient, which facilitates the replacement and daily maintenance of fluid impact pin 12. For example, in FIGS. 8 to 11, fluid impact pin 12 is made of metal wire, such as, steel wire. Furthermore, the head 122 is formed by bending the lower end of the fluid impact pin 12, thus the manufacturing process of the fluid impact pin 12 is simplified. It should be noted that, the fluid impact pin 12 may be non-detachably connected with the nozzle body 11, such as by welding or by glue.

As shown in FIG. 8 to FIG. 14, the nozzle body 11 includes a connector 11*a*, an upper housing 11*b*, a middle housing 11*c* and a lower housing 11*d*. The connector 11*a* successively passes through the upper housing 11*b* and the middle housing 11*c* and is then threaded with the lower housing 11*d*, and the upper housing 11*b* and the middle housing 11*c* are clamped by the connector 11*a* and the lower housing 11*d*. A sealing ring 11*e* is respectively arranged between the connector 11*a* and the upper housing 11*b*, between the upper housing 11*b* and the middle housing 11*c*, and between the middle housing 11*c* and the lower housing 11*d*. The inclined spray channel 113 is formed in the upper housing 11*b* and the middle housing 11*c*, the liquid inlet channel 111 is formed in the connector 11*a* and the lower housing 11*d*, the lower nozzle hole 114 is formed in the lower housing 11*d*, the inclined upper nozzle hole 113 is formed in the upper housing 11*b*, and the output end 32 of the elastic braided hose 30 is assembled and connected with the connector 10*a*, as shown in FIG. 13. In these configurations, the assembly and disassembly of all components inside the nozzle body 11 is convenient. Optionally, as an embodiment, each of the connector 11*a*, the upper housing 11*b*, the middle housing 11*c* and the lower housing 11*d* is rotatable, to facilitate the manufacturing.

Figure 17:
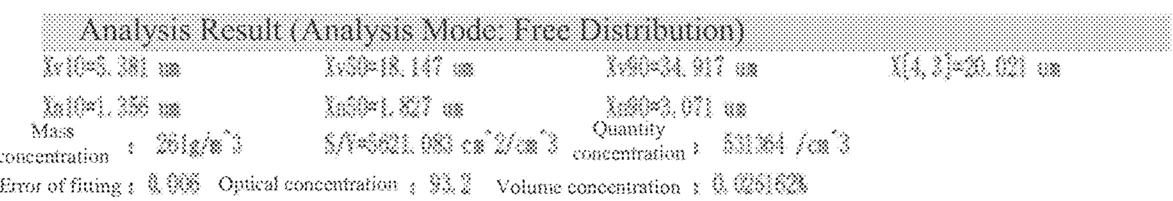
FIG. 17 is a particle size distribution diagram of aerosol atomized by the pressurized nebulizer of the invention, under experimental conditions of the motor speed of peristaltic pump being 420 rpm, the model of elastic braided hose being BM-CT-3.65-150B, and the conveying flow rate of the peristaltic pump being 72.5 mL/min.
Figure 17:
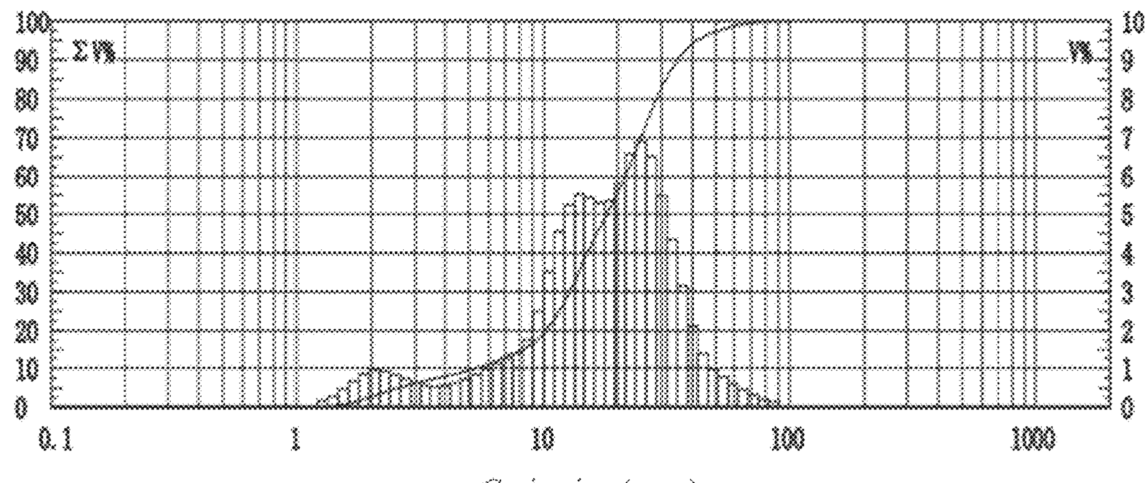

Referring to FIG. 17, atomization was tested by the pressurized nebulizer according to the present invention under the experimental conditions that the motor speed of peristaltic pump 20 is 420 rpm, the model of elastic braided hose 30 is BM-CT-3.65-150B (with an outer diameter of 3.65 mm, a unilateral wall thickness of 0.9 mm, and an inner diameter of 1.85 mm), and the conveying flow rate of the peristaltic pump 20 is 72.5 mL/min, and the distribution of particle size of aerosol atomized by the pressurized nebulizer 100 is shown. It seen that, the particle size of the atomized aerosol is distributed from 1 to 100 microns, and mainly distributed between 30 and 50 microns (including the two endpoint values of 30 and 50 microns), which conforms to the distribution rule of middle particle size accounting for a large proportion while the particle size on both sides accounting for a small proportion.

Figure 18:
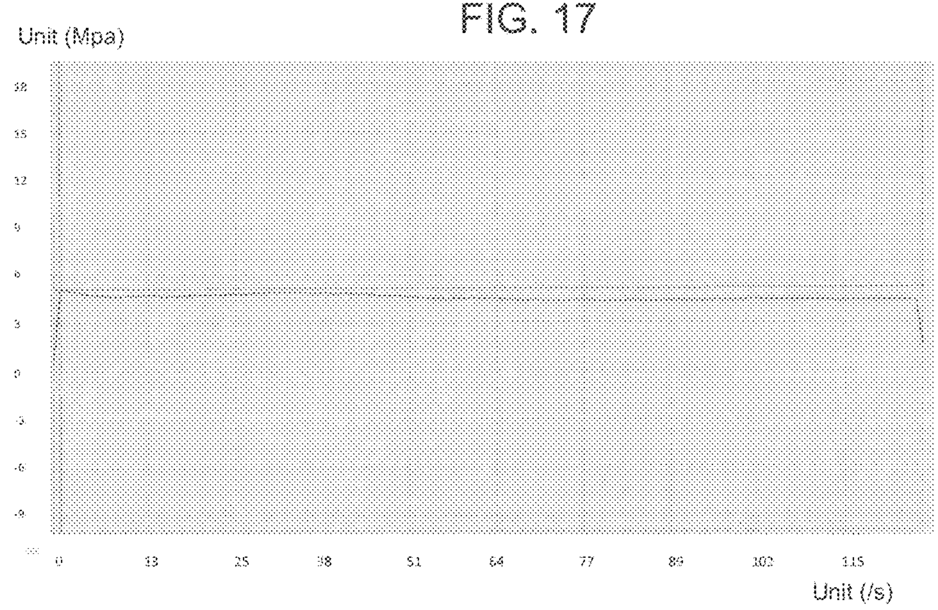
FIG. 18 is a pressure trend diagram of the liquid in the output end of the elastic braided hose, when the pressurized nebulizer of the invention works under experimental conditions of the motor speed of peristaltic pump being 420 rpm, the model of elastic braided hose being BM-CT-3.65-150B, and the minimum clearance P being 1.60 mm.

Referring to FIG. 18, atomization was tested by the pressurized nebulizer according to the present invention under the experimental conditions that the motor speed of peristaltic pump 20 is 420 rpm, the model of elastic braided hose 30 is BM-CT-3.65-150B, and the minimum clearance P is 1.60 mm, and the pressure trend of the liquid in the output end 32 of the elastic braided hose 30 of the pressurized nebulizer 100 is shown. As shown, the liquid in the elastic braided hose 30 is jetted from the output end 32 to the nozzle 10 at a pressure greater than 3 MPa and less than or equal to 6 MPa.

Figure 19:
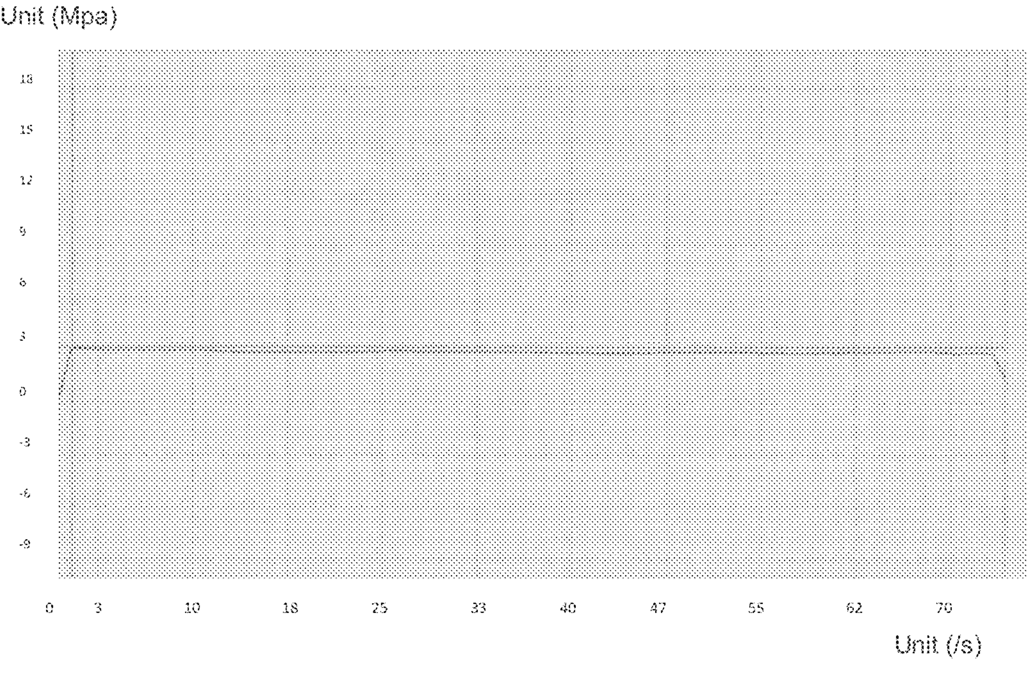
FIG. 19 is a pressure trend diagram of the liquid in the output end of the elastic braided hose, when the pressurized nebulizer of the invention works under experimental conditions of the motor speed of peristaltic pump being 420 rpm, the model of elastic braided hose being BM-CT-3.65-150B, and the minimum clearance P being 1.50 mm.

Referring to FIG. 19, atomization was tested by the pressurized nebulizer according to the present invention under the experimental conditions that the motor speed of peristaltic pump 20 is 420 rpm, the model of elastic braided hose 30 is BM-CT-3.65-150B, and the minimum clearance P is 1.50 mm, and the pressure trend of the liquid in the output end 32 of the elastic braided hose 30 of the pressurized nebulizer 100 is shown. As shown, the liquid in the elastic braided hose 30 is jetted from the output end 32 to the nozzle 10 at a pressure greater than 2 MPa and less than or equal to 3 MPa.

Figure 20:
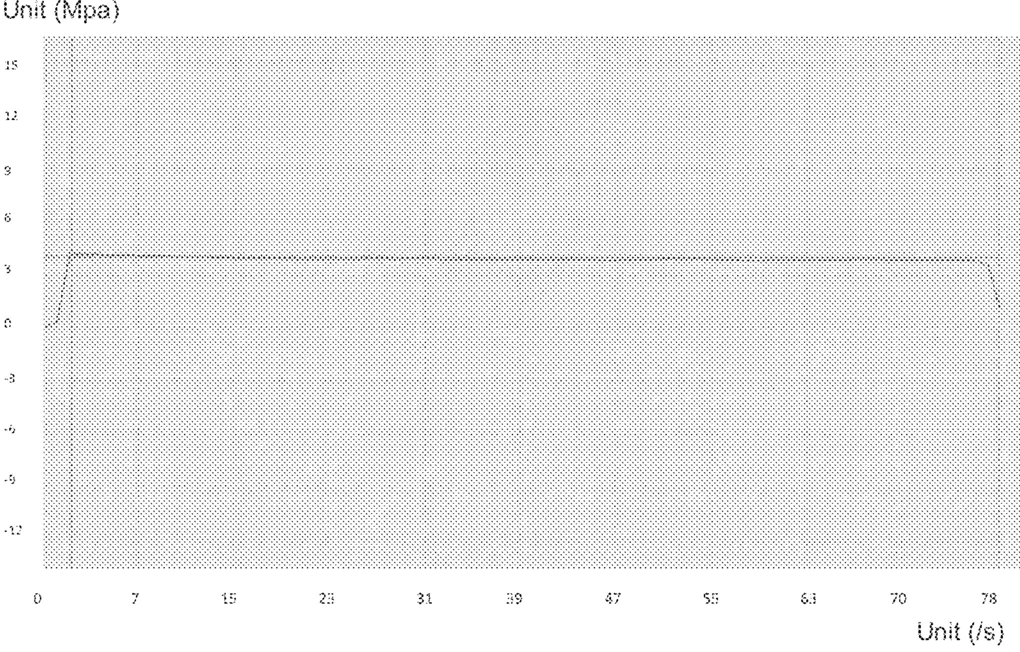
FIG. 20 is a pressure trend diagram of the liquid in the output end of the elastic braided hose, when the pressurized nebulizer of the invention works under experimental conditions of the motor speed of peristaltic pump being 420 rpm, the model of elastic braided hose being BM-CT-3.65-150B, and the minimum clearance P being 1.65 mm.

Referring to FIG. 20, atomization was tested by the pressurized nebulizer according to the present invention under the experimental conditions that the motor speed of peristaltic pump 20 is 420 rpm, the model of elastic braided hose 30 is BM-CT-3.65-150B, and the minimum clearance P is 1.65 mm, and the pressure trend of the liquid in the output end 32 of the elastic braided hose 30 of the pressurized nebulizer 100 is shown. As shown, the liquid in the elastic braided hose 30 is jetted from the output end 32 to the nozzle 10 at a pressure greater than 2 MPa and less than or equal to 5 MPa.

Figure 21:
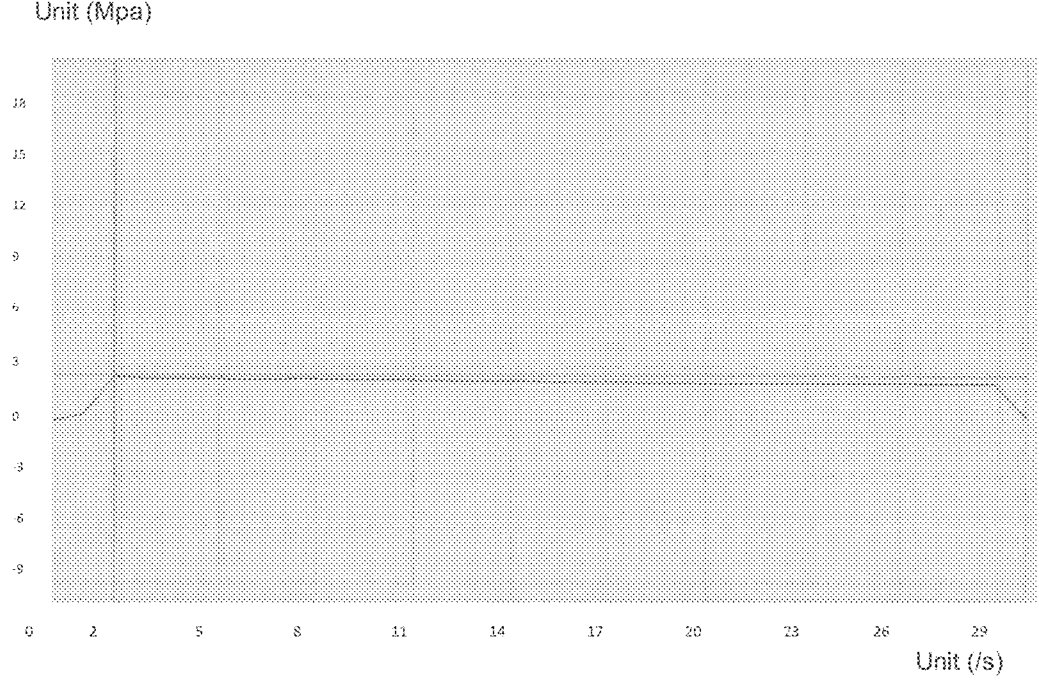
FIG. 21 is a pressure trend diagram of the liquid in the output end of the elastic braided hose, when the pressurized nebulizer of the invention works under experimental conditions of the motor speed of peristaltic pump being 420 rpm, the model of elastic braided hose being BM-CT-3.65-150B, and the minimum clearance P being 1.70 mm.

Referring to FIG. 21, atomization was tested by the pressurized nebulizer according to the present invention under the experimental conditions that the motor speed of peristaltic pump 20 is 420 rpm, the model of elastic braided hose 30 is BM-CT-3.65-150B, and the minimum clearance P is 1.70 mm, and the pressure trend of the liquid in the output end 32 of the elastic braided hose 30 of the pressurized nebulizer 100 is shown. As shown, the liquid in the elastic braided hose 30 is jetted from the output end 32 to the nozzle 10 at a pressure greater than 2 MPa and less than or equal to 3 MPa.

In conjunction with the attached drawings, the working principle of the pressurized nebulizer 100 of the invention is explained. The rollers 214 in the peristaltic pump 20 are driven by the motor 22 to rotate clockwise, so that each roller 214 has the working stroke $S_1$ and the non-working stroke $S_2$. In the working stroke $S_1$, the liquid in the container 40 is sucked into the elastic braided hose 30 under the movement of the rollers 214, and then conveyed to the output end 32 of the elastic braided hose 30 at a pressure greater than or equal to 2 MPa, and finally sprayed out from the nozzle 10, so as to spray the atomization. Specifically, by overcoming the elastic force of the first elastic part 16, the upper thimble 13 is pushed by the liquid in the nozzle 10 to slide downward, so that the liquid inlet channel 111 at above is opened, causing the liquid in the elastic braided hose 30 enters the liquid inlet channel 111. Meanwhile, the first elastic component 16 is compressed and deformed due to the downward sliding of the upper thimble 13 slides downward. Then, the liquid fed into the liquid inlet channel 111 will be conveyed in two ways: a first part of the liquid passes through the connected channel 141 of the lower thimble 14, then jetted downward from the lower nozzle hole 112, and then impacted on the fluid impact pin 12 to spray in all directions, as shown in the arrows fluid impact pin 12 near the fluid impact pin 12 in FIG. 12; a second part of the liquid passes through inclined spray channel 113 and the middle channel 151, and then jetted from the inclined upper nozzle hole 114, as shown in the arrows on the inclined upper nozzle hole 114 in FIG. 14. In such a way, a spray atomization at the spray nozzle 10 is obtained.

Compared with the prior art, the pressurized nebulizer 100 of the invention is configured with a peristaltic pump 20 and an elastic braided hose 30 with a maximum pressure endurance value greater than or equal to 2 MPa, and the minimum clearance P between the roller 214 and the mating part 212 when switching to the limit position is: $1.5T \leq P \leq 1.9T$. Based on the above configurations and the cooperation of the peristaltic pump 20 and the elastic braided hose 30, the liquid sucked into the elastic braided hose 30 at the input end 31 can be conveyed to the output end 32 of the elastic braided hose 30 at a pressure greater than or equal to 2 MPa, and then sprayed out at the nozzle 10 in forms of aerosol particles. Therefore, the pressure nebulizer 100 of the invention can avoid the contact pollution of the peristaltic pump 20 on the liquid by means of the cooperation of the peristaltic pump 20 and the elastic braided hose 30, and a continuous and stable output of the aerosol particles from the nozzle 10 may be ensured under the power of the peristaltic pump 20, thereby achieving accurate accuracy, safety and reliability and convenient operation. In addition, the present invention further overcomes a preconception in the art that "person skilled in the art generally believes that the existing peristaltic pump may only applicable to complex liquid quantitative distribution to achieve high-precision flow transmission control, but not applicable to the pressurization of liquid".

In the existing peristaltic pump, it's ordinarily believed that the peristaltic pump is only applicable to complex liquid quantitative distribution to achieve high-precision flow transmission control. Therefore, the peristaltic pump provided with a pump tube and pump head is generally configured to adapt to this purpose. Usually the pump tube is silicone tube or rubber tube with the maximum pressure withstand value of not exceeding about 5 atmospheric pressures. Further, in order to prevent from damaging the pump tube due to excessive pressure of the liquid in the pump tube exceeding the maximum pressure value, a large clearance is formed between the roller in the existing peristaltic pump and the inner wall of the pump head. It's seen that, the overall structures of the existing peristaltic pump including the material of the pump tube, the maximum pressure withstand value of the pump tube and the clearance of the pump head are designed and configured for the low-pressure quantitative conveying of ordinary liquid. Therefore, it's generally believed in the art that, the existing peristaltic pumps are not applicable to the pressurization of liquid.

In the pressurized nebulizer 100 of the invention, the peristaltic pump 20 and the elastic braided hose 30 whose maximum pressure withstand value is greater than or equal to 2 MPa are applied, and a minimum clearance P formed between the roller and the mating part is $1.5T \leq P \leq 1.9T$ when the roller is switched to the limit position, thereby achieving high pressure conveying to the nozzle 10 at a pressure greater than or equal to 2 MPa, and there is no contact between the liquid and the peristaltic pump.

It is worth noting that, in the peristaltic pump 20, the rotating base 213 is driven by the motor 22 to rotate, that is, the installation between the rotating base 213 and the motor 22 is well known in this field, which is not described here. In addition, four the rollers 214 are arranged in a circle on the rotating base 213 at intervals, and preferably in centrally symmetrical arrangement, as shown in FIG. 5. Optionally, the rollers 214 with other quantities also may be configured, such as one or more rollers 214. In addition, the fixing part 211 and the mating part 212 in the peristaltic pump 20 are also well-known in the field. It's important that, the maximum pressure withstand value of the elastic braided hose 30 should be greater than or equal to the maximum pressure value of the liquid output from the elastic braided hose 30 under the work of the peristaltic pump 20.

In addition, according to the actual needs, the pressurized nebulizer 100 of the invention may not include the container 40, the Luer taper 50, the needle connector 60, the guider 70 and the rod 34, namely it is not limited to that shown in FIGS. 1 and 2.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A pressurized nebulizer, comprising a nozzle, a peristaltic pump, and an elastic braided hose with a maximum pressure endurance value greater than or equal to 2 MPa;

wherein the peristaltic pump has a pump head which comprises a fixing part, a mating part that is movable relative to the fixing part along an up-down direction of the pump head, a rotating base that is rotatable on the fixing part, and a roller assembled on the rotating base; the rotating base has a circular trajectory when rotating along the rotating base, and the roller is extended beyond the rotating base along a radial direction of the circular trajectory;

when the mating part and the fixing part are in a closed state, the elastic braided hose is arranged between the mating part and the fixing part, and jointly between the mating part and the roller; the elastic braided hose comprises an input end and an output end located outside the pump head, and the output end of the elastic braided hose is connected with the nozzle;

the roller during a rotation with the rotating base has a working stroke of contacting and extruding the elastic braided hose and a non-working stroke of non-contacting with the elastic braided hose; in the working stroke, the roller has a limit position of extruding the elastic braided hose to a limit state, and a movement of the roller in the working stroke is configured to cause liquid coming from the input end of the elastic braided hose to be conveyed to the output end of the elastic braided hose at a pressure greater than or equal to 2 MPa, and then sprayed out at the nozzle; wherein, when the roller is switched to the limit position, a minimum clearance formed between the roller and the mating part is $1.5T \leq P \leq 1.9T$, where T denotes a unilateral wall thickness of the elastic braided hose, and P denotes the minimum clearance.

2. The pressurized nebulizer according to claim 1, further comprising a container for holding the liquid, wherein the input end of the elastic braided hose is connected with the container, and the roller in the working stroke is configured to cause the liquid in the container to be sucked into the elastic braided hose.

3. The pressurized nebulizer according to claim 2, further comprising a Luer taper and a needle connector, wherein the Luer taper is connected with the input end of the elastic braided hose, and one end of the Luer taper away from the input end of the elastic braided hose is connected with the needle connector, and the needle connector is selectively inserted into or pulled out of the container.

4. The pressurized nebulizer according to claim 1, further comprising a guider including a hollow channel, wherein the nozzle is configured to pass through the guider or pull out from the guider along the hollow channel.

5. The pressurized nebulizer according to claim 1, wherein one or more holding assemblies are provided in the pump head; when two holding assemblies are configured, the two holding assemblies are arranged symmetrically in the pump head for holding two opposite sides of the pump head.

6. The pressurized nebulizer according to claim 5, wherein each holding assembly comprises a clamping part arranged on one of the fixing part and the mating part, the clamping part comprises a main body and a first elastic arm and a second elastic arm arranged on the main body, the first elastic arm and the second elastic arm together define a clamping channel and an opening for allowing the elastic braided hose to press into or move out of the clamping channel along an up-down direction of the pump head.

7. The pressurized nebulizer according to claim 6, wherein the holding assembly further comprises a hold-down part arranged on another of the fixing part and the mating part, the hold-down part is provided with a toothed structure facing the clamping part, the toothed structure is staggered with the clamping part along a left-right direction of the pump head, and the toothed structure is pressed against the elastic braided hose along the up-down direction of the pump head.

8. The pressurized nebulizer according to claim 1, wherein the nozzle comprises a nozzle body, a fluid impact pin, an upper thimble, a lower thimble, an inclined thimble, a first elastic component and a second elastic component; the nozzle body is provided with a liquid inlet channel for allowing the liquid from the output end of the elastic braided hose, a lower nozzle hole for ejecting the liquid, an inclined spray channel located beside the liquid inlet channel and laterally communicated with the liquid inlet channel, and an inclined upper nozzle hole connected with the inclined spray channel.

9. The pressurized nebulizer according to claim 8, wherein the inclined spray channel, the inclined thimble, the second elastic component and the inclined upper nozzle hole together constitute an inclined spray unit; when multiple inclined spray units are configured, the inclined spray units arranged around the liquid inlet channel.

10. The pressurized nebulizer according to claim 8, wherein the fluid impact pin comprises a leg assembled on the nozzle body and a head fixed on the leg, the head is aligned with the lower nozzle hole along an up-down direction of the nozzle body.

11. The pressurized nebulizer according to claim 8, wherein the upper thimble, the lower thimble and the first elastic component are located in the liquid inlet channel, the first elastic component is further pressed between the upper thimble and the lower thimble, and the first elastic component is configured to always have a tendency to drive the upper thimble to move upward to a first position of blocking the liquid inlet channel from above, and further always have a tendency to drive the lower thimble to move downward to a second position of blocking the liquid inlet channel from underneath; the lower thimble is provided with a connected channel that enables the liquid inlet channel and the lower nozzle hole to be communicated when the lower thimble is in the second position; the second elastic component and the inclined thimble are located in the inclined spray channel, and the second elastic component is configured to always have a tendency to drive the inclined thimble to move upward to a third position of blocking the inclined spray channel from above; and the inclined thimble is provided with an intermediate channel to maintain communication between the inclined spray channel and the inclined nozzle hole when the inclined thimble is in the third position.

12. The pressurized nebulizer according to claim 11, wherein the intermediate channel comprises multiple intermediate channels arranged in a center symmetry on the inclined thimble, each of the intermediate channels is a first notch structure that runs through a side surface and a top surface of the inclined thimble, and a bottom wall of the first notch structure is defined with a first inclined plane which is inclined upward from the side surface of the inclined thimble to the top surface of the inclined thimble.

13. The pressurized nebulizer according to claim 11, wherein the connected channel comprises multiple connected channels arranged in a center symmetry on the lower thimble, each of the connected channels is a second notch that runs through a side surface and a bottom surface of the lower thimble, a top wall of the second notch is defined with a second inclined plane which is inclined downward from the side surface of the lower thimble to a bottom surface of the lower thimble.

14. The pressurized nebulizer according to claim 8, wherein center lines of the liquid inlet channel and the lower nozzle hole coincide, and center lines of the inclined spray channel and the inclined upper nozzle hole coincide, and an angle between the center line of the liquid inlet channel and the center line of the inclined spray channel ranges from 15 to 30 degrees.

15. The pressurized nebulizer according to claim 8, wherein the nozzle body comprises a connector, an upper housing, a middle housing and a lower housing, and the connector successively passes through the upper housing and the middle housing and is then threaded with the lower housing, the upper housing and the lower housing are clamped by the connector and the middle housing.

16. The pressurized nebulizer according to claim 15, wherein a sealing ring is respectively arranged between the connector and the upper housing, between the upper housing and the middle housing, and between the middle housing and the lower housing.

17. The pressurized nebulizer according to claim 15, wherein the inclined spray channel is formed in the upper housing and the middle housing, the liquid inlet channel is formed in the connector and the lower housing, the lower nozzle hole is formed in the lower housing, the inclined upper nozzle hole is formed in the upper housing, and the output end of the elastic braided hose is connected with the connector.

18. The pressurized nebulizer according to claim 1, wherein the movement of the roller in the working stroke is configured to cause liquid coming from the input end of the elastic braided hose to be conveyed to the output end of the elastic braided hose at a pressure greater than or equal to 2 MPa and less than or equal to 6 Mpa, and the maximum pressure endurance value of the elastic braided hose is greater than or equal to 2 MPa and less than or equal to 8 Mpa.

* * * * *